US009676777B2

United States Patent
Abe et al.

(10) Patent No.: US 9,676,777 B2
(45) Date of Patent: Jun. 13, 2017

(54) COMPOUNDS USEFUL FOR PRODUCING AN OPTICALLY ACTIVE DIAZABICYCLOOCTANE COMPOUND

(71) Applicant: Meiji Seika Pharma Co., Ltd., Tokyo (JP)

(72) Inventors: Takao Abe, Kanagawa (JP); Masayuki Okue, Kanagawa (JP); Yoshiaki Sakamaki, Kanagawa (JP)

(73) Assignee: MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 15/007,906

(22) Filed: Jan. 27, 2016

(65) Prior Publication Data

US 2016/0137645 A1    May 19, 2016

Related U.S. Application Data

(60) Continuation of application No. 14/676,179, filed on Apr. 1, 2015, now Pat. No. 9,284,273, which is a division of application No. 14/287,380, filed on May 27, 2014, now Pat. No. 9,035,062, which is a division of application No. 13/173,002, filed on Jun. 30, 2011, now Pat. No. 8,772,490.

(60) Provisional application No. 61/459,954, filed on Dec. 22, 2010.

(51) Int. Cl.
*C07D 471/08* (2006.01)
*C07D 211/60* (2006.01)

(52) U.S. Cl.
CPC .......... *C07D 471/08* (2013.01); *C07D 211/60* (2013.01); *C07B 2200/07* (2013.01)

(58) Field of Classification Search
CPC .................................................. C07D 471/08
USPC ........................................ 546/121, 223, 242
See application file for complete search history.

(56) References Cited

U.S. PATENT DOCUMENTS

| | | | |
|---|---|---|---|
| 7,112,592 B2 | 9/2006 | Lampilas et al. |
| 7,612,087 B2 | 11/2009 | Aszodi et al. |
| 7,638,529 B2 | 12/2009 | Lampilas et al. |
| 7,732,610 B2 | 6/2010 | Lampilas et al. |
| 8,178,554 B2 | 5/2012 | Lampilas et al. |
| 8,288,553 B2 | 10/2012 | Priour et al. |
| 8,471,025 B2 | 6/2013 | Dedhiya et al. |
| 8,487,093 B2 | 7/2013 | Blizzard et al. |
| 8,796,257 B2 | 8/2014 | Maiti et al. |
| 8,822,450 B2 | 9/2014 | Patel et al. |
| 8,829,191 B2 | 9/2014 | Ronsheim et al. |
| 8,835,455 B2 | 9/2014 | Dedhiya et al. |
| 8,877,743 B2 | 11/2014 | Maiti et al. |
| 8,969,566 B2 | 3/2015 | Ronsheim et al. |
| 9,062,053 B2 | 6/2015 | Dedhiya et al. |
| 9,181,250 B2 | 11/2015 | Abe et al. |
| 9,284,314 B2 | 3/2016 | Ronsheim et al. |
| 2003/0199541 A1 | 10/2003 | Lampilas et al. |
| 2003/0220521 A1 | 11/2003 | Reitz et al. |
| 2005/0020572 A1 | 1/2005 | Aszodi et al. |
| 2005/0245505 A1 | 11/2005 | Aszodi et al. |
| 2006/0046995 A1 | 3/2006 | Lampilas et al. |
| 2006/0189652 A1 | 8/2006 | Lampilas et al. |
| 2007/0299108 A1 | 12/2007 | Aszodi et al. |
| 2009/0215747 A1 | 8/2009 | Aszodi et al. |
| 2010/0048528 A1 | 2/2010 | Aszodi et al. |
| 2010/0087648 A1 | 4/2010 | Lampilas et al. |
| 2010/0197928 A1 | 8/2010 | Priour et al. |
| 2011/0021772 A1 | 1/2011 | Lampilas et al. |
| 2011/0046102 A1 | 2/2011 | Ledoussal et al. |
| 2011/0152311 A1 | 6/2011 | Dedhiya et al. |
| 2011/0213147 A1 | 9/2011 | Lampilas et al. |
| 2011/0245254 A1 | 10/2011 | Aszodi et al. |
| 2011/0294777 A1 | 12/2011 | Blizzard et al. |
| 2013/0012712 A1 | 1/2013 | Priour et al. |
| 2013/0225554 A1 | 8/2013 | Maiti et al. |
| 2013/0267480 A1 | 10/2013 | Dedhiya et al. |
| 2013/0274475 A1 | 10/2013 | Mangion et al. |

(Continued)

FOREIGN PATENT DOCUMENTS

| | | |
|---|---|---|
| EP | 0213595 A2 | 3/1987 |
| JP | 2004505088 A | 2/2004 |

(Continued)

OTHER PUBLICATIONS

U.S. Appl. No. 14/872,988, Title: "Beta-Lactamase Inhibitor and Process for Preparing the Same", filed Oct. 1, 2015, First Named Inventor: Takao Abe.

(Continued)

*Primary Examiner* — Niloofar Rahmani
(74) *Attorney, Agent, or Firm* — Holtz, Holtz & Volek PC

(57) ABSTRACT

An optically active (2S,5R)-7-oxo-1,6-diazabicyclo[3.2.1] octane-2-carboxylic acid compound defined by the following formula (F):

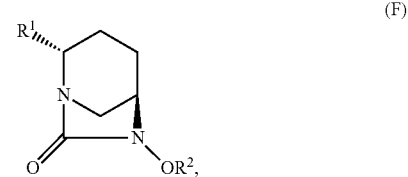

wherein $R^1$ represents $CO_2R$, $CO_2M$, or $CONH_2$, wherein R represents an allyl group or a benzyl group, and M represents a hydrogen atom, an inorganic cation, or an organic cation; and $R^2$ represents a benzyl group or an allyl group.

7 Claims, No Drawings

(56) References Cited

U.S. PATENT DOCUMENTS

| | | | |
|---|---|---|---|
| 2013/0281359 A1 | 10/2013 | Maiti et al. |
| 2014/0221341 A1 | 8/2014 | Maiti et al. |
| 2014/0288051 A1 | 9/2014 | Malti et al. |
| 2015/0246920 A1 | 9/2015 | Dedhiya et al. |
| 2016/0024090 A1 | 1/2016 | Abe et al. |

FOREIGN PATENT DOCUMENTS

| | | | |
|---|---|---|---|
| JP | 2005518333 A | 6/2005 |
| JP | 2005523897 A | 8/2005 |
| JP | 2010138206 A | 6/2010 |
| JP | 4515704 B2 | 8/2010 |
| JP | 2010539147 A | 12/2010 |
| JP | 2011510012 A | 3/2011 |
| JP | 2011518871 A | 6/2011 |
| JP | 2011207900 A | 10/2011 |
| JP | 2012504593 A | 2/2012 |
| JP | 5038509 B2 | 10/2012 |
| WO | 0210172 A1 | 2/2002 |
| WO | 02100860 A2 | 12/2002 |
| WO | 03063864 A2 | 8/2003 |
| WO | 2009090320 A1 | 7/2009 |
| WO | 2009091856 A2 | 7/2009 |
| WO | 2009133442 A1 | 11/2009 |
| WO | 2010038115 A1 | 4/2010 |
| WO | 2010126820 A2 | 11/2010 |
| WO | 2011042560 A1 | 4/2011 |
| WO | 2012086241 A1 | 6/2012 |
| WO | 2012172368 A1 | 12/2012 |
| WO | 2013030735 A1 | 3/2013 |
| WO | 2013180197 A1 | 12/2013 |

OTHER PUBLICATIONS

U.S. Appl. No. 15/023,976, Title: "Process for Producing Diazabicyclooctane Derivative and Intermediate Thereof", filed Mar. 22, 2016, First Named Inventor: Takao Abe.

U.S. Appl. No. 15/027,956; First Named Inventor: Takao Abe; Title: "Crystalline Forms of Diazabicyclooctane Derivative and Production Process Thereof"; filed Apr. 7, 2016.

Mangion et al, "A Concise Synthesis of a β-Lactamase Inhibitor", Organic Letters, 2011, vol. 13, No. 20, pp. 5480-5483.

Noriaki Hirayama, Yuki Kagobutsu Kessho Sakusei Handbook—Genri to Know-how-, Maruzen Co., Ltd., Jul. 25, 2008, pp. 57-84.

Brown et al, "Some Active Derivatives of Penicillin", Applied Microbiology 1969, vol. 17, No. 3, pp. 339-343.

Pettit, et al., "8-Hydroxy-5-trifluoromethylquinoline", Journal of Chemical Society (1954), 3852-3854.

Jung, JC et al., Diastereoselective synthesis of (2S,5S)- and (2S,5S)-N-benzyloxycarbonyl-5-hydroxypipecolic acids from trans-4-hydroxy-L-proline, Tetrahedron Asymmetry, 2006, 17(17), pp. 2497-2486.

Baldwin, JE et al., "A Novel Entry to Carbenoid Species via β-Ketosulfoxonium Ylides", Journal of the Chemical Society, Chemical Communications, 1993, pp. 1434-1435.

Viangion, IK et al., "Iridium-Catalyzed X-H Insertions of Sulfoxonium Ylides", Organic Letters, 2009, 11(16), pp. 3566-3569.

Dolence, EK et al., "Synthesis and siderophone activity of albomycin-like peptides derived from N5-acetyl-N5-hydroxy-L-ornithine", Journal of Medicinal Chemistry, 1991, 34(3), pp. 956-968.

King, FE et al., "The Chemistry of Extractives from Hardwoods, Part III. Baikiain, an Amino-acid Present in Baikiaea plurijuga", Journal of the Chemical Society, 1950, pp. 3590-3597.

Witkop, B et al., "The Configuration of 5-Hydroxypipecolic Acid From Dates", Journal of the American Chemical Society, 1957, 79(1), pp. 192-197.

Freed, ME et al., "Synthesis of 5-Ketopipecolic Acid from Glutamic Acid", The Journal of Organic Chemistry, 1960, 25(12), pp. 2105-2107.

Extended European Search Report dated Sep. 4, 2014, issued in counterpart European Application No. 11850585.8.

Cerfontain, et al., "Sulfur Trioxide", Encyclopedia of Reagents for Organic Synthesis, vol. 7, edited by Leo A. Paquette, 1995, John Wiley and Sons, pp. 4699-4702.

Knight, "N-Hydroxysuccinimide", Encyclopedia of Reagents for Organic Synthesis, vol. 4, Edited by Leo A. Paquette, 1995, John Wiley and Sons, pp: 2780-2781.

McIntosh, "Sulfur Troxide-1, 4-Dioxane", Encyclopedia of Reagents for Organic Synthesis, vol. 7, Edited by Leo A. Paquette, 1995, John Wiley and Sons, pp. 4702-4703.

Tidwell, "Sulfur Trioxide-Pyridine", Encyclopedia of Reagents for Organic Synthesis, vol. 7, Edited by Leo A. Paquette, 1995, John Wiley and Sons, pp. 4703-4704.

Caira, "Crystalline Polymorphism of Organic Compounds", Topics in Current Chemistry, Springer, Berlin, DE, vol. 198, Jan. 1, 1998: pp. 163-208.

COMPOUNDS USEFUL FOR PRODUCING AN OPTICALLY ACTIVE DIAZABICYCLOOCTANE COMPOUND

CROSS-REFERENCE TO RELATED APPLICATIONS

This application is a continuation application of Ser. No. 14/676,179 filed on Apr. 1, 2015 (U.S. Pat. No. 9,284,273), which is a divisional application of application Ser. No. 14/287,380 filed on May 27, 2014 (U.S. Pat. No. 9,035,062), which is a divisional application of application Ser. No. 13/173,002 filed on Jun. 30, 2011 (U.S. Pat. No. 8,772,490). This application claims the benefit under 35 USC 119(e)(i) of provisional application Ser. No. 61/459,954 filed on Dec. 22, 2010. The entire contents of each of application Ser. No. 14/676,179, application Ser. No. 14/287,380, application Ser. No. 13/173,002 and provisional application Ser. No. 61/459,954 are incorporated by reference herein.

FIELD OF THE INVENTION

The present invention relates to an optically active diazabicyclooctane derivative defined by formula (F) below, which is useful as a pharmaceutical intermediate for β-lactamase inhibitor, and a process for preparing the same.

[Chemical formula 1]

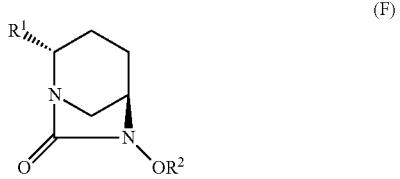

(F)

In formula (F) above, $R^1$ represents $CO_2R$, $CO_2M$, or $CONH_2$, wherein R represents a methyl group, a tert-butyl group, an allyl group, a benzyl group, or a 2,5-dioxopyrrolidin-1-yl group, and M represents a hydrogen atom, an inorganic cation, or an organic cation; and $R^2$ represents a benzyl group or an allyl group.

BACKGROUND ART

Penicillins and cephalosporins are β-lactam antibiotics which are most widely and frequently used in the clinic. However, the development of resistance to β-lactam antibiotics by various pathogens severely has had a damaging effect on maintaining the effective treatment of bacterial infections. The most significant known mechanism related to the development of bacterial resistance is the production of class A, C, and D β-lactamases having a serine residue at the active center. These enzymes decompose the β-lactam antibiotic, resulting in the loss of the antimicrobial activities. Class A β-lactamases preferentially hydrolyze penicillins while class C β-lactamases have a substrate profile favoring cephalosporins. As commercially available β-lactamase inhibitors, clavulanic acid, sulbactam, and tazobactam are known, and these inhibitors are effective mainly against class A β-lactamase producing bacteria, and used as a mixture with a penicillin antibiotic. However, 250 types or more of β-lactamases have been reported to date, and among them, in addition to the expansion of class C β-lactamases as well as extended-spectrum β-lactamase (ESBL) belonging to class A and D β-lactamases, further resistant bacteria which produce class A KPC-2 β-lactamase decomposing even carbapenem as a last resort for β-lactam antibiotic is being considered as a problem. Although the development of a novel inhibitor is strongly demanded as the commercially available inhibitors are ineffective against these β-lactamases and potential inhibitors are disclosed, there are only a few candidates under development.

In recent years, U.S. Pat. No. 7,112,592 (patent document 1) and U.S. Pat. No. 7,612,087 (patent document 2) have disclosed that a racemic diazabicyclooctane derivative is a promising compound in the treatment of an infectious disease as a non-β-lactam antimicrobial or β-lactamase inhibitor, and have demonstrated the working Example of a racemic diazabicyclooctane derivatives from a racemic cis-5-hydroxypiperidine-2-carboxylic acid derivative and those biological activity.

With respect to the optically active diazabicyclooctane derivative, in working Example 1 of WO2009/091856 A2 (patent document 3) and WO2010/126820 A2 (patent document 4), a process for preparing a derivative having a specific amide side chain is described. Further, working Example 1 of patent document 3 has merely a description of a chemical name of (2S,5R)-6-(benzyloxy)-7-oxo-1,6-diazabicyclo[3.2.1]octane-2-carboxylic acid as an intermediate for research, and similarly, in WO2009/133442 A1 (patent document 5), a chemical name of (2S,5R)-6-hydroxy-7-oxo-1,6-diazabicyclo[3.2.1]octane-2-carboxamide is described, and in EP 2135959 A1 (patent document 6), a chemical name of (2S,5R)-1,6-diazabicyclo[3.2.1]octane-2-carboxamide, 7-oxo-6-(sulfoxy)-monosodium salt is described.

On the other hand, with respect to (2S,5S)-5-hydroxypiperidine-2-carboxylic acid and (2S,5R)-5-(benzyloxyamino)piperidine-2-carboxylic acid, which are considered as an important starting material of the diazabicyclooctane derivative, and derivatives thereof, one having an ester side chain has been reported in Tetrahedron Asymmetry 2006, 17(17), 2479-2486 (non-patent document 2) and J. Chem. Soc., Chem. Commun., 1993, 1434 (non-patent document 3), and one having an amide side chain has been reported in working Example 1C of patent document 3, Org. Lett., 2009, 11(16), 3566-3569 (non-patent document 3), and patent document 4. Further, as a process for preparing a derivative not through a (2S,5S)-5-hydroxypiperidine-2-carboxylic acid derivative, US 2010/197928 A (patent document 7) discloses a process for preparing benzyl (2S)-5-(benzyloxyimino)piperidine-2-carboxylate or benzyl (2S,5R/S)-5-(benzyloxyamino)piperidine-2-carboxylare.

[Patent document 1] U.S. Pat. No. 7,112,592
[Patent document 2] U.S. Pat. No. 7,612,087
[Patent document 3] International Publication No. 2009/091856 A2
[Patent document 4] International Publication No. 2010/126820 A2
[Patent document 5] International Publication No. 2009/133442 A1

[Patent document 6] European Patent Application Publication No. 2135959 A1

[Patent document 7] U.S. Patent Application Publication No. 2010/197928 A1

[Non-patent document 1] Jung, J C.; Avery, M A. "Diastereoselective synthesis of (2S,5S)- and (2S,5R)—N-benzyloxycarbonyl-5-hydroxypipecolic acids from trans-4-hydroxy-L-proline" Tetrahedron Asymmetry 2006, 17(17), 2479-2486.

[Non-patent document 2] Baldwin, J E.; Adlington, R M.; Godfrey, C R A.; Gollins, D W.; Vaughan, J G. "A Novel Entry to Carbenoid Species via β-Ketosulfoxonium Ylides" Journal of the Chemical Society Chemical Communications 1993, 1434-1435.

[Non-patent document 3] Mangion, I K.; Nwamba, I K.; Shevlin, M.; Huffman M A. "Iridium-Catalyzed X-H Insertions of Sulfoxonium Ylides" Organic Letters 2009, 11(16), 3566-3569.

[Non-patent document 4] Dolence, E K.; Lin, C E.; Miller, M J.; Payne, S M. "Synthesis and siderophore activity of albomycin-like peptides derived from N5-acetyl-N5-hydroxy-L-ornithine" Journal of Medicinal Chemistry 1991, 34(3), 956-968.

[Non-patent document 5] King, F E.; King, T J.; Warwick, A J. "The Chemistry of Extractives from Hardwoods. Part III. Baikiain, an Amino-acid Present in Baikiaea plurijuga" Journal of the Chemical Society 1950, 3590-3597.

[Non-patent document 6] Witkop, B.; Folts, C M. "The Configuration of 5-Hydroxypipecolic Acid from Dates" Journal of the American Chemical Society 1957, 79(1), 192-197.

[Non-patent document 7] Freed, M E.; Day A R. "Synthesis of 5-Ketopipecolic Acid from Glutamic Acid" The Journal of Organic Chemistry 1960, 25(12), 2105-2107.

DISCLOSURE OF THE INVENTION

Problems to be Solved by the Invention

However, the prior arts about the β-lactamase inhibitor having a diazabicyclooctane skeleton, particularly about the diazabicyclooctane derivative as a common intermediate used for preparing the β-lactamase inhibitor have a number of technical problems to be solved as mentioned below.

Patent documents 1 and 2 show the working example of the racemic diazabicyclooctane derivative, but do not disclose a process for preparing the optically active diazabicyclooctane derivative and a process for optical resolution of the derivative and data from instrumental analyses for the optically active compound, particularly data for demonstrating the preparation of the optically active compound, such as angle of rotation, and there has not been demonstrated that the optically active compound is actually obtained in an independent form.

In the processes described in patent documents 1 and 2, the selection of the carboxylate ester protecting group at the 2-position is inappropriate, and therefore allyl trans-5-(benzyloxyamino)piperidine-2-carboxylate represented by formula (b) in the reaction scheme below as a precursor for the intermediate and allyl trans-6-(benzyloxy)-7-oxo-1,6-diazabicyclo[3.2.1]octane-2-carboxylate represented by formula (d) below as a desired important intermediate cannot be efficiently prepared. In the field of drug manufacturing, when a compound has an asymmetric carbon atom, it is desired that only a single enantiomer is selectively prepared according to the object, but it is not easy to directly apply the processes of patent documents 1 and 2 to the separately obtained optically active (2S,5S)-5-hydroxypiperidine-2-carboxylic acid derivative, or to optically resolve the mass-produced racemic diazabicyclooctane derivative and supply the resultant optically active compound to the research and drug manufacturing application.

[Chemical formula 2]

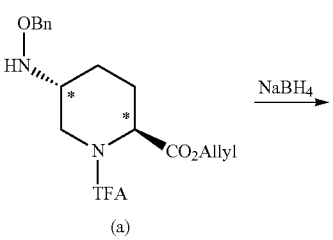

(a)

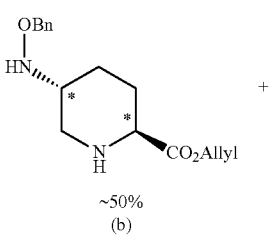

~50%

(b)

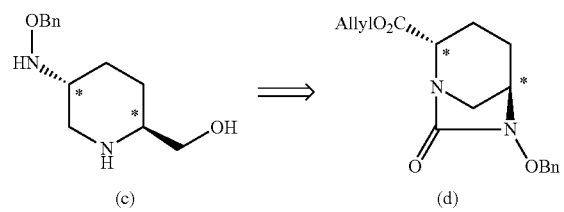

(c)                                    (d)

In the above reaction scheme, TFA represents a 2,2,2-trifluoroacetyl group, NaBH$_4$ represents sodium boron hydride, and BnO represents a benzyloxy group.

In patent documents 3, 5, and 6, chemical names of (2S,5R)-6-(benzyloxy)-7-oxo-1,6-diazabicyclo[3.2.1]octane-2-carboxylic acid, (2S,5R)-6-hydroxy-7-oxo-1,6-diazabicyclo[3.2.1]octane-2-carboxamide, (1R,2S,5R)-1,6-diazabicyclo[3.2.1]octane-2-carboxamide, and 7-oxo-6-(sulfoxy)-monosodium salt as optically active compounds are described, but, with respect to the process for preparing them, merely reference is made to patent documents 1 and 2 which disclose a process for preparing the racemic modification.

Only patent documents 3 and 4 demonstrate a process for preparing the optically active diazabicyclooctane derivative, but this process is specific only to a compound having a specific amide side chain at the 2-position, and thus the value of the application of the process to the common intermediate is not suggested. Further, an attempt was made to apply the introduction reaction of a benzyloxyamino group through a para-trifluoromethylbenzenesulfonyloxy group or the intramolecular urea formation reaction using triphosgene disclosed in patent documents 3 and 4 to a compound having an ester side chain at the 2-position, but stereoselectivity of the benzyloxyamino group was not observed and the substantial intramolecular urea formation reaction did not proceed which indicates that the above reactions cannot be directly applied to the compound having an ester side chain at the 2-position.

[Chemical formula 3]

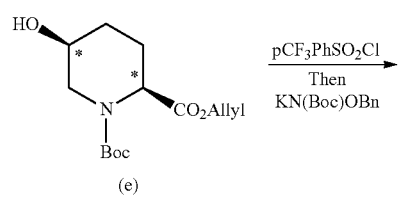

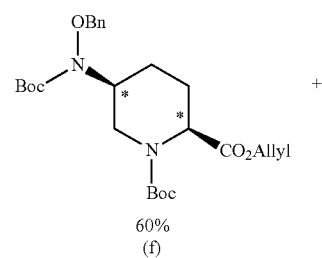

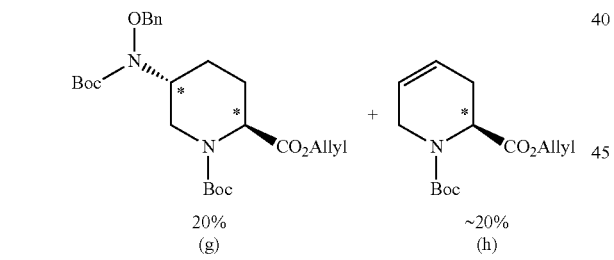

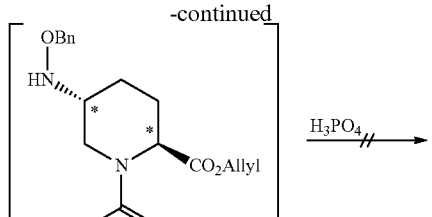

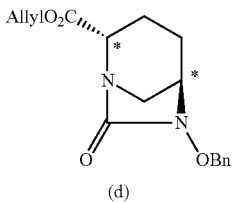

In the above reaction scheme, Boc represents a tert-butoxycarbonyl group, $pCF_3PhSO_2Cl$ represents para-trifluoromethylbenzenesulfonyl chloride, KN(Boc)OBn represents potassium N-tert-butoxycarbonylbenzyloxyamide, and BnO represents a benzyloxy group; the compounds of formulae (f) and (g) shown in the above reaction scheme cannot be directly separated, and therefore the structures of them were determined by NMR after deprotection of Boc group, intramolecular urea formation using diphosgene, and isolation of the product.

Further, patent document 4 also demonstrates a process for preparing (2S,5S)-di-tert-butyl 5-hydroxypiperidine-1,2-dicarboxylate, but selective deprotection of the tert-butoxycarbonyl group and the tert-butyl ester on the piperidine ring is difficult, and further selective tert-butyl esterification of only the carboxyl group separately from the hydroxyl group is not easy after deprotection of all the protective groups. Therefore, it is difficult to industrially use the disclosed compound as a starting material directly for the common intermediate aimed at by the present inventors.

In patent document 7, the amount of the trimethylsulfoxonium iodide used in the preparation of the important starting material is not disclosed, and it is unclear whether the method is a practicable process without a side reaction, such as decomposition of the ester or possibility of racemization due to an excess reagent. In actual fact, data from an instrumental analysis showing the planar configuration of the formed ketosulfoxonium ylide compound is described, but with respect to the compounds including the products formed in the subsequent steps, data from an instrumental analysis showing the optical purity, particularly such as angle of rotation, is not demonstrated. Further, the stereoselectivity of the benzyloxyamino group at the 5-position is as low as cis-trans=1:1 and thus the process is not efficient. The formed cis-trans isomer is present in the form of a mixture which is difficult to separate, and there is no description showing that a diazabicyclooctane derivative can be actually derived from the prepared mixture.

As described above, a process for preparing an optically active diazabicyclooctane derivative, particularly a 2-carboxylic acid or ester derivative useful as a common intermediate has not been disclosed hitherto. Therefore, the development of an easily practicable process for preparing an optically active diazabicyclooctane derivative having a carboxylic acid and ester side chain, which can be used as a common intermediate, has been desired for the research of a more highly effective novel compound and pharmaceutical development.

In this situation, the present inventors have made extensive and intensive studies with a view toward developing an optically active diazabicyclooctane derivative, particularly a 2-carboxylic acid and ester derivative, which is useful as a pharmaceutical intermediate for β-lactamase inhibitor, and an easily practicable process for preparing the same. As a result, it has been found that, by using as a starting material a (2S,5S)-5-hydroxypiperidine-2-carboxylic acid derivative which is a known compound, an optically active diazabicyclooctane derivative can be industrially supplied with excellent reproductivity in high yield through a relatively short process without lowering the optical purity of the derivative, and further that the optically active diazabicyclooctane derivative obtained by such a process can be used as a pharmaceutical intermediate for β-lactamase inhibitor, and the present invention has been completed.

Means to Solve the Problems

Specifically, the present invention is directed to an optically active (2S,5R)-7-oxo-1,6-diazabicyclo[3.2.1]octane-2-carboxylic acid derivative defined by the following formula (F):

[Chemical formula 4]

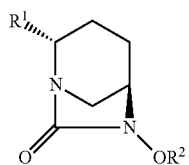

wherein:
$R^1$ represents $CO_2R$, $CO_2M$, or $CONH_2$,
wherein R represents a methyl group, a tert-butyl group, an allyl group, a benzyl group, or a 2,5-dioxopyrrolidin-1-yl group, and
M represents a hydrogen atom, an inorganic cation, or an organic cation; and
$R^2$ represents a benzyl group or an allyl group.

The present invention is also directed to a process for preparing the compound defined by the formula (F) above, wherein the process comprises subjecting a compound represented by formula (E) below to intramolecular urea formation, and then subjecting the resultant compound represented by formula (F1) below to at least one of the steps below:

[Chemical formula 5]

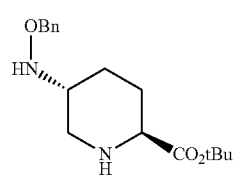

wherein Bn represents a benzyl group, and tBu represents a tert-butyl group,

[Chemical formula 6]

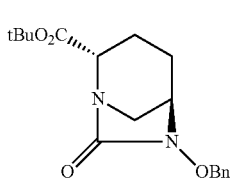

wherein Bn represents a benzyl group, and tBu represents a tert-butyl group, step a for cleaving the ester, step b for converting the compound to the form of a salt of an inorganic cation or organic cation, step c for treating the compound with an acid to convert the compound to a free acid, step d for performing carbamoylation for the carboxylic acid, step e for converting the carboxylic acid to an ester, step f for removing the benzyl group of the benzyloxy group at the 6-position, and step g for converting the group at the 6-position to allyloxy.

Further, the present invention is also directed to a process for preparing the compound represented by the formula (E) above, wherein the process comprises subjecting a compound represented by formula (B) below to trifluoroacetylation, and reacting the resultant compound represented by formula (C) below with benzyloxyamine in the presence of a hydroxyl group activating agent, and subjecting the resultant compound represented by formula (D) below to detrifluoroacetylation:

[Chemical formula 7]

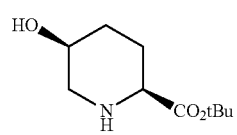

wherein tBu represents a tert-butyl group,

[Chemical formula 8]

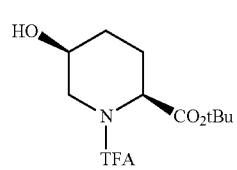

wherein tBu represents a tert-butyl group, and TFA represents a trifluoroacetyl group,

[Chemical formula 9]

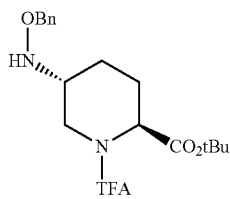

(D)

wherein Bn represents a benzyl group, tBu represents a tert-butyl group, and TFA represents a trifluoroacetyl group.

Furthermore, the present invention is also directed to an intermediate compound for use in preparing the compound represented by the formula (F) above, i.e., compounds represented by the following formulae (B), (C), (D), and (E):

[Chemical formula 10]

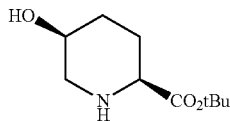

(B)

wherein tBu represents a tert-butyl group,

[Chemical formula 11]

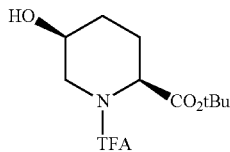

(C)

wherein tBu represents a tert-butyl group, and TFA represents a trifluoroacetyl group,

[Chemical formula 12]

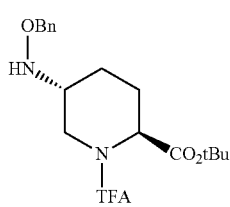

(D)

wherein Bn represents a benzyl group, tBu represents a tert-butyl group, and TFA represents a trifluoroacetyl group,

[Chemical formula 13]

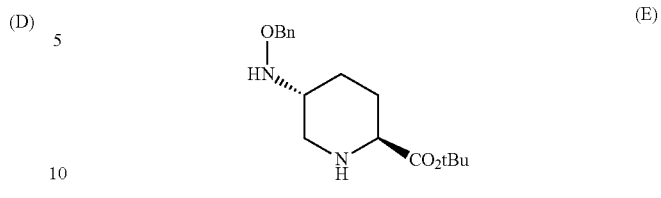

(E)

wherein Bn represents a benzyl group, and tBu represents a tert-butyl group.

Effect of the Invention

By the process for preparing an optically active diazabicyclooctane derivative provided by the present invention, an optically active (2S,5R)-7-oxo-1,6-diazabicyclo[3.2.1]octane-2-carboxylic acid derivative can be industrially supplied with excellent reproducibility in high yield through a relatively short process without lowering the optical purity of the derivative. Further, thus obtained optically active (2S,5R)-7-oxo-1,6-diazabicyclo[3.2.1]octane-2-carboxylic acid derivative of the present invention is easily crystallized, and hence is easy to handle and can be used in the mass-production of an optically active compound for a β-lactamase inhibitor having a diazabicyclooctane skeleton, or can be used as an important intermediate in the research and mass-production of a more highly effective novel β-lactamase inhibitor, and therefore is especially excellent as an intermediate for the industrial production.

BEST MODE FOR CARRYING OUT THE INVENTION

As mentioned above, the present invention is directed to an optically active (2S,5R)-7-oxo-1,6-diazabicyclo[3.2.1]octane-2-carboxylic acid derivative defined by the following formula (F):

[Chemical formula 14]

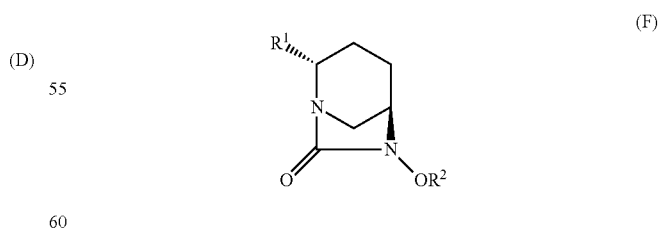

(F)

wherein: $R^1$ represents $CO_2R$, $CO_2M$, or $CONH_2$,
wherein R represents a methyl group, a tert-butyl group, an allyl group, a benzyl group, or a 2,5-dioxopyrrolidin-1-yl group, and M represents a hydrogen atom, an inorganic cation, or an organic cation; and $R^2$ represents a benzyl group or an allyl group.

The inorganic cation is, e.g., sodium, potassium, lithium, or calcium, and is preferably sodium, potassium, or calcium. The organic cation is an ammonium salt formed from an amine, such as trimethylamine, triethylamine, cyclohexylamine, or dicyclohexylamine; or a quaternary ammonium salt, such as tetramethylammonium, tetraethylammonium, tetrabutylammonium, or triethylbenzylammonium, and is preferably a cyclohexylammonium salt.

Preferred examples of the compounds defined by formula (F) include the following compounds:
(2S,5R)-tert-butyl 6-(benzyloxy)-7-oxo-1,6-diazabicyclo[3.2.1]octane-2-carboxylate,
(2S,5R)-6-(benzyloxy)-7-oxo-1,6-diazabicyclo[3.2.1]octane-2-carboxylic acid cyclohexylamine salt,
(2S,5R)-6-(benzyloxy)-7-oxo-1,6-diazabicyclo[3.2.1]octane-2-carboxylic acid,
(2S,5R)-6-(benzyloxy)-7-oxo-1,6-diazabicyclo[3.2.1]octane-2-carboxamide,
(2S,5R)-methyl 6-(benzyloxy)-7-oxo-1,6-diazabicyclo[3.2.1]octane-2-carboxylate,
(2S,5R)-allyl 6-(benzyloxy)-7-oxo-1,6-diazabicyclo[3.2.1]octane-2-carboxylate,
(2S,5R)-benzyl 6-(benzyloxy)-7-oxo-1,6-diazabicyclo[3.2.1]octane-2-carboxylate,
(2S,5R)-2,5-dioxopyrrolidin-1-yl 6-(benzyloxy)-7-oxo-1,6-diazabicyclo[3.2.1]octane-2-carboxylate,
(2S,5R)-tert-butyl 6-(allyloxy)-7-oxo-1,6-diazabicyclo[3.2.1]octane-2-carboxylate,
(2S,5R)-6-(allyloxy)-7-oxo-1,6-diazabicyclo[3.2.1]octane-2-carboxylic acid cyclohexylamine salt,
(2S,5R)-6-(allyloxy)-7-oxo-1,6-diazabicyclo[3.2.1]octane-2-carboxylic acid, and
(2S,5R)-benzyl 6-(allyloxy)-7-oxo-1,6-diazabicyclo[3.2.1]octane-2-carboxylate.

The optically active (2S,5R)-7-oxo-1,6-diazabicyclo[3.2.1]octane-2-carboxylic acid derivative defined by general formula (F), which is newly provided by the present invention, can be prepared from a compound of formula (E), and the compound of formula (E) can be obtained from a compound of formula (A), which is a known compound, as a starting material basically in accordance with the process shown by the chemical reaction scheme below.

[Chemical formula 15]

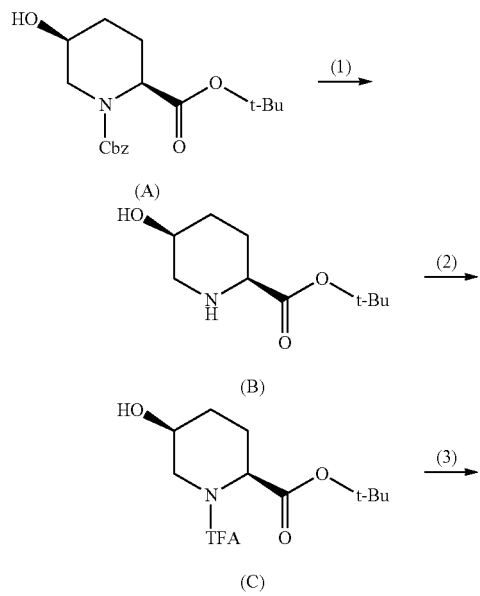

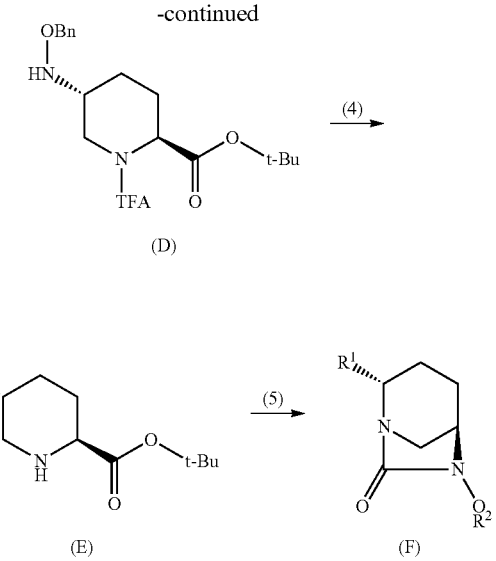

In the above chemical reaction scheme, Cbz represents a benzyloxycarbonyl group, t-Bu represents a tert-butyl group, TFA represents a 2,2,2-trifluoroacetyl group, OBn represents a benzyloxy group, $R^2$ represents a benzyl group or an allyl group, preferably a benzyl group, and the figures in parentheses indicate the number of the respective steps.

Specifically, the compound defined by formula (F) of the present invention can be obtained through the first step for removing the benzyloxycarbonyl group of a compound represented by formula (A) to derive a compound represented by formula (B), the second step for subjecting the nitrogen atom of the piperidine to trifluoroacetylation to derive a compound represented by formula (C), the third step for substituting the hydroxyl group at the 5-position with benzyloxyamine in the presence of a hydroxyl group activating agent to derive a compound represented by formula (D), the fourth step for removing the trifluoroacetyl group to derive a compound represented by formula (E), and the fifth step for conducting intramolecular urea formation and then conversion of $R^1$, $R^2$ side chains to derive an optically active (2S,5R)-7-oxo-1,6-diazabicyclo[3.2.1]octane-2-carboxylic acid derivative defined by formula (F).

The selection of the tert-butyl ester of the compound represented by formula (A), which can used as a starting material in the present invention, has a very important role in selectively removing the trifluoroacetyl group of the compound represented by formula (D). In addition, the benzyloxycarbonyl group which is a protecting group for NH on the piperidine ring can be deblocked easily separately from the tert-butyl ester, and hence the compound of formula (A) is an optimum starting material as a precursor for the compound represented by formula (B). Further, the process of the present invention is an extremely useful process such that a trans-oxyamino compound can be selectively prepared without forming an unnecessary cis-benzyloxyamino compound. That is, the above-mentioned process using the compound represented by formula (A) as a starting material is extremely useful also as a process for efficiently preparing optically active (2S,5R)-tert-butyl 5-(benzyloxyamino)piperidine-2-carboxylate represented by formula (E).

The compound represented by formula (A), which is used as a starting material in the process of the present invention, can be prepared by the process reported in non-patent document 1, but can also be prepared by the more efficient process which is shown by the reaction scheme below from a known compound represented by formula (k) below described in non-patent document 4.

[Chemical formula 16]

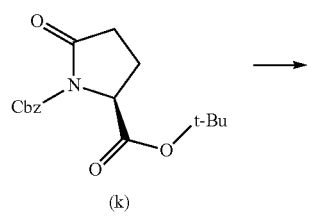

(k)

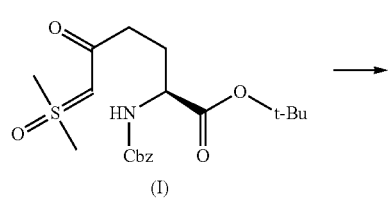

(I)

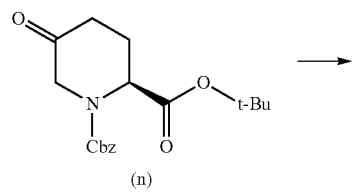

(n)

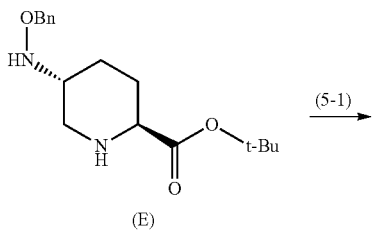

(A)

In the above chemical reaction scheme, Cbz represents a benzyloxycarbonyl group, and t-Bu represents a tert-butyl group.

[Chemical formula 18]

The optically active (2S,5R)-7-oxo-1,6-diazabicyclo[3.2.1]octane-2-carboxylic acid derivative defined by formula (F), which is provided by the present invention, can be prepared by, for example, a process which comprises subjecting a compound represented by formula (E) to intramolecular urea formation, and then subjecting the resultant compound represented by formula (F1) to at least one of the steps: a step (step a) for cleaving the ester, a step (step b) for converting the compound to the form of a salt of an inorganic cation or organic cation, a step (step c) for treating the compound with an acid to convert the compound to a free acid, a step (step d) for performing carbamoylation for the carboxylic acid, a step (step e) for converting the carboxylic acid to an ester, a step (step f) for removing the benzyl group of the benzyloxy group at the 6-position, and a step (step g) for converting the group at the 6-position to allyloxy.

[Chemical formula 17]

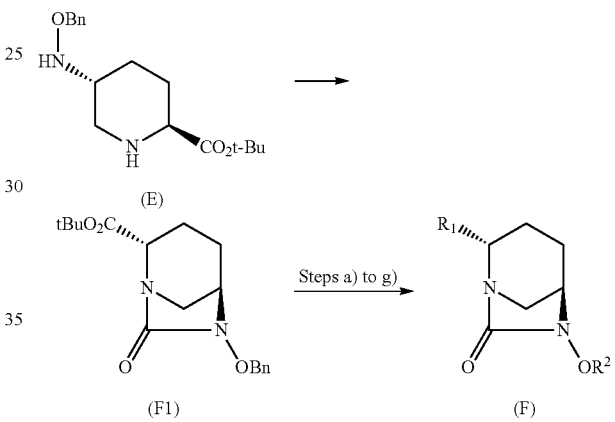

(E)          (F1)          (F)

The symbols shown in the formulae are as defined above.

In the specific embodiments of the above-mentioned process for obtaining the compound defined by formula (F) from the compound defined by formula (E), as shown below, the compound represented by formula (F) in each embodiment can be obtained through step (5-1) for intramolecular urea formation and then at least one of steps (5-2) to (5-8). More specifically, these steps can be conducted in accordance with the process shown by the chemical reaction scheme below.

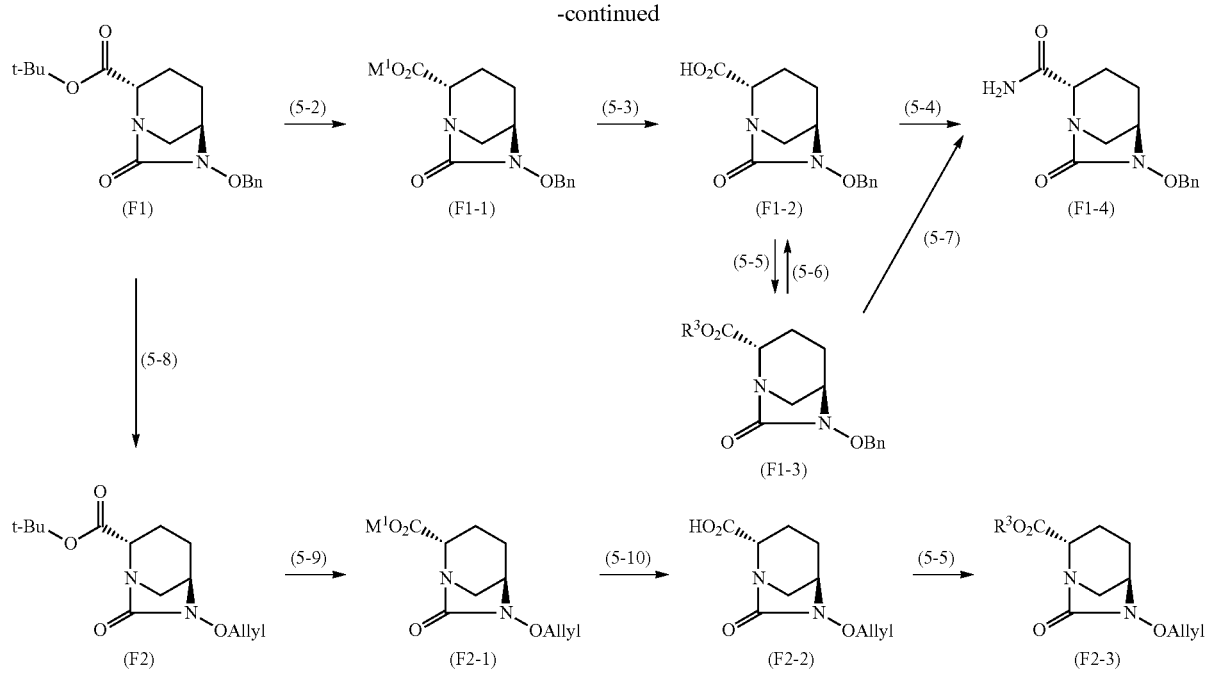

In the above reaction scheme, OBn represents a benzyloxy group, t-Bu represents a tert-butyl group, $M^1$ represents cyclohexyl ammonium, $R^3$ represents a methyl group, an allyl group, a benzyl group, or a 2,5-dioxopyrrolidin-1-yl group, OAllyl represents an allyloxy group, and the figures in parentheses indicate the number of the respective steps.

Specifically, the process according to the above-shown embodiment of the present invention comprises 5-1 step for subjecting a compound represented by formula (E) to intramolecular urea formation to obtain a compound represented by formula (F1), 5-2 step for cleaving the tert-butyl ester to obtain a cyclohexyl ammonium salt represented by formula (F1-1), 5-3 step for treating the cyclohexylammonium salt with an acid to obtain a free acid represented by formula (F1-2), 5-4 or 5-5 step for deriving formula (F1-4) or formula (F1-3) from the carboxylic acid, or 5-8 step for removing the benzyl group from formula (F1) and converting it to an allyl group to derive formula (F2), 5-9 and 5-10 steps for cleaving the tert-butyl ester to obtain formulae (F2-1) and (F2-2), and 5-5 step for deriving formula (F2-3) from the carboxylic acid.

Among the compound defined by formula (F) of the present invention obtained by the above-mentioned process of the present invention, (2S,5R)-tert-butyl 6-(benzyloxy)-7-oxo-1,6-diazabicyclo[3.2.1]octane-2-carboxylate, (2S,5R)-methyl 6-(benzyloxy)-7-oxo-1,6-diazabicyclo[3.2.1]octane-2-carboxylate, (2S,5R)-allyl 6-(benzyloxy)-7-oxo-1,6-diazabicyclo[3.2.1]octane-2-carboxylate, (2S,5R)-6-(benzyloxy)-7-oxo-1,6-diazabicyclo[3.2.1]octane-2-carboxylic acid cyclohexylammonium salt, (2S,5R)-6-(benzyloxy)-7-oxo-1,6-diazabicyclo[3,2,1]octane-2-carboxylic acid, and (2S,5R)-6-(benzyloxy)-7-oxo-1,6-diazabicyclo[3.2.1]octane-2-carboxamide, which are respectively represented by formulae (F1), (F1-3a), (F1-3b), (F1-1a), (F1-2) and (F1-4) below, can be individually obtained in the form of a crystal of the optically active diazabicyclooctane derivative, and therefore have an advantage in that they are easy to isolate, purify, store, and transport. This indicates that the present invention is an industrially useful invention.

[Chemical formula 19]

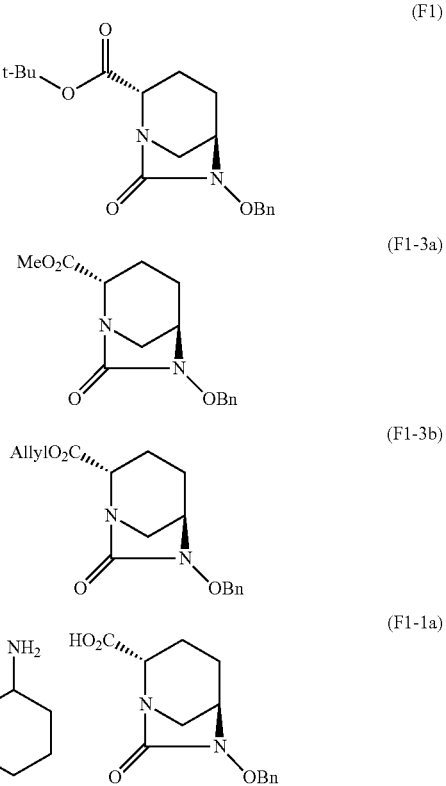

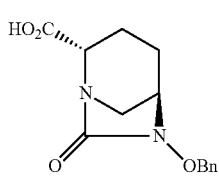

(F1-2)

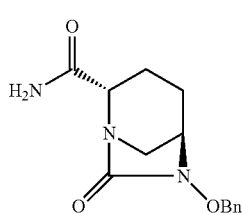

(F1-4)

In the above formulae, t-Bu represents a tert-butyl group, OBn represents a benzyloxy group, and Me represents a methyl group.

(2S,5R)-tert-butyl 6-(benzyloxy)-7-oxo-1,6-diazabicyclo[3.2.1]octane-2-carboxylate represented by formula (F1) is present in the form of a crystal having characteristic peaks appearing at lattice spacings (d) of 11.56, 10.96, 6.55, 6.00, 5.79, 5.56, 5.47, 5.25, 4.90, 4.35, 4.23, and 3.86 Å, and it is especially preferred that the compound is obtained as a crystal with high purity, which is easy to handle, by isolation or purification particularly on an industrial scale.

(2S,5R)-methyl 6-(benzyloxy)-7-oxo-1,6-diazabicyclo[3.2.1]octane-2-carboxylate represented by formula (F1-3a) is present in the form of a crystal which exhibits a powder X-ray diffraction pattern having characteristic peaks appearing at lattice spacings (d) of 10.39, 5.86, 5.69, 5.34, 4.81, 4.44, 3.98, 3.78, 3.11, 3.03, 2.93, and 2.77 Å, and it is especially preferred that the compound is obtained as a crystal with high purity, which is easy to handle, by isolation or purification particularly on an industrial scale.

(2S,5R)-allyl 6-(benzyloxy)-7-oxo-1,6-diazabicyclo[3.2.1]octane-2-carboxylate represented by formula (F1-3b) is present in the form of a crystal which exhibits a powder X-ray diffraction pattern having characteristic peaks appearing at lattice spacings of 14.72, 4.91, 4.46, 4.24, and 3.67 Å, and it is especially preferred that the compound is obtained as a crystal with high purity, which is easy to handle, by isolation or purification particularly on an industrial scale.

(2S,5R)-6-(benzyloxy)-7-oxo-1,6-diazabicyclo[3.2.1]octane-2-carboxylic acid cyclohexylammonium salt represented by formula (F1-1a) is present in the form of a crystal which exhibits a powder X-ray diffraction pattern having characteristic peaks appearing at lattice spacings (d) of 9.95, 8.45, 6.26, 5.87, 5.52, 5.22, 5.10, 4.96, 4.73, 4.54, 4.16, 3.93, and 3.55 Å, and it is especially preferred that the compound is obtained as a crystal with high purity, which is easy to handle, by isolation or purification particularly on an industrial scale.

(2S,5R)-6-(benzyloxy)-7-oxo-1,6-diazabicyclo[3.2.1]octane-2-carboxylic acid represented by formula (F1-2) is present in the form of a crystal which exhibits a powder X-ray diffraction pattern having characteristic peaks appearing at lattice spacings (d) 8.19, 7.14, 6.64, 6.29, 5.60, 5.21, 4.91, 4.60, 4.21, 3.69, 3.45, and 3.13 Å, and it is especially preferred that the compound is obtained as a crystal with high purity, which is easy to handle, by isolation or purification particularly on an industrial scale.

Further, (2S,5R)-6-(benzyloxy)-7-oxo-1,6-diazabicyclo[3.2.1]octane-2-carboxamide represented by formula (F1-4) is present in the form of a crystal which exhibits a powder X-ray diffraction pattern having characteristic peaks appearing at lattice spacings (d) of 13.06, 6.52, 5.14, 4.74, 4.63, 4.34, 3.85, and 3.72 Å, and it is especially preferred that the compound is obtained as a crystal with high purity, which is easy to handle, by isolation or purification particularly on an industrial scale.

Hereinbelow, the process provided by the present invention, which comprises a series of steps for obtaining an optically active diazabicyclooctane derivative defined by formula (F) from the compound defined by formula (A) as a starting material, will be described in more detail.

Synthesis of Compound of Formula (B) from Compound of Formula (A)

The benzyloxycarbonyl group of (2S,5S)-1-benzyl 2-tert-butyl 5-hydroxypiperidine-1,2-dicarboxylate, which is used as a starting material in the present invention, and which is represented by formula (A):

[Chemical formula 20]

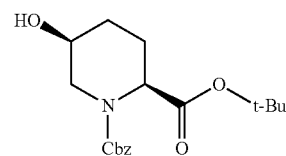

(A)

wherein, in formula (A) above, Cbz represents a benzyloxycarbonyl group, and t-Bu represents a tert-butyl group, is removed by a catalytic hydrogenation reaction in a hydrogen gas atmosphere in the presence of a catalyst to obtain (2S,5S)-tert-butyl 5-hydroxypiperidine-2-carboxylate represented by formula (B):

[Chemical formula 21]

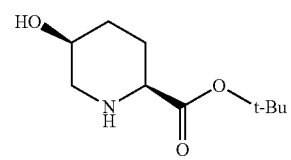

(B)

wherein, in formula (B) above, t-Bu represents a tert-butyl group.

With respect to the catalyst used in the reaction, an arbitrary hydrogenation catalyst can be used, but, for example, platinum oxide, palladium oxide, palladium black, or palladium-carbon can be preferably used. The catalyst can be used in the range of from 0.05 to 1 w/w in terms of a weight ratio of the catalyst to the compound of formula (A). The hydrogen pressure can be from atmospheric pressure to 0.5 MPa.

The solvent used in the reaction can be selected from water, methanol, ethanol, propanol, isopropanol, butanol, ether, diisopropyl ether, ethyl acetate, butyl acetate, toluene, tetrahydrofuran, and 1,4-dioxane, and these solvents can be used alone or in combination.

Preferably, a catalyst selected from platinum oxide, palladium oxide, palladium black, and palladium-carbon can be used in a weight ratio of 0.05 to 0.5 w/w in methanol or ethanol.

More preferably, palladium-carbon in a weight ratio of 0.05 to 0.25 w/w can be used as a catalyst in ethanol.

The compound represented by formula (B) prepared in the first step can be isolated, for example, as a free base by employing, after completion of the reaction, typical work-up procedure means generally used in the organic chemistry, such as filtration for catalyst, solvent concentration, solvent exchange, salt formation, and crystallization, and used in the next step, or can be used in the next step without being purified after the post-treatment.

Synthesis of Compound of Formula (C) from Compound of Formula (B)

The above-obtained compound of formula (B) is treated with a trifluoroacetylating agent in the presence of a base to obtain (2S,5S)-tert-butyl 5-hydroxy-1-(2,2,2-trifluoroacetyl)piperidine-2-carboxylate represented by formula (C):

[Chemical formula 22]

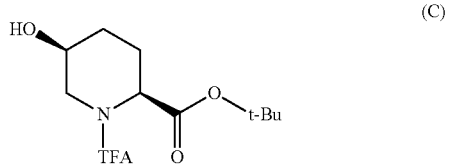

(C)

wherein, in formula (C) above, TFA represents a 2,2,2-trifluoroacetyl group, and t-Bu represents a tert-butyl group.

Specifically, the trifluoroacetylation of the compound represented by formula (B) is conducted by dissolving the compound of formula (B) in an appropriate solvent and reacting it with an excess amount of a trifluoroacetylating agent in the presence of an excess amount of a base to form a 1,5-ditrifluoroacetyl compound and then cleaving only the trifluoroacetyl group at the 5-position.

The base used in the reaction can be selected from inorganic bases, such as sodium hydrogencarbonate, potassium hydrogencarbonate, sodium carbonate, potassium carbonate, sodium hydroxide, and potassium hydroxide, and organic bases, such as triethylamine, diisopropylethylamine, tributylamine, 1,8-diazabicyclo[5.4.0]undec-7-ene, pyridine, 2-picoline, and 2,6-lutidine, and is used in an amount in the range of from 2 to 6 molar equivalents relative to the compound of formula (B).

The trifluoroacetylating agent can be selected from trifluoroacetic acid, ethyl trifluoroacetate, trifluoroacetic anhydride, trifluoroacetyl chloride, trifluoroacetylsuccinimide ester, trifluoroacetylbenzotriazole ester, trifluoroacetylpentafluorophenyl ester, 2-trifluoroacetoxypyridine, and dodecyl trifluorothioacetate, and can be used in an amount in the range of from 1.5 to 3 molar equivalents relative to the compound of formula (B). The trifluoroacetylation reaction is conducted at a temperature in the range of from −30 to +50° C. The cleavage of the trifluoroacetoxy group at the 5-position can be conducted by, after the post-treatment for the trifluoroacetylation or immediately after the trifluoroacetylation, stirring the mixture in water or an alcohol solvent, such as methanol or ethanol, in the presence of the above-mentioned base at room temperature or while heating.

The solvent used in the reaction can be selected from water, methanol, ethanol, propanol, isopropanol, butanol, dichloromethane, 1,2-dichloroethane, chloroform, ether, diisopropyl ether, ethyl acetate, butyl acetate, tetrahydrofuran, 1,4-dioxane, N,N-dimethylformamide, and N,N-dimethylacetamide, and these solvents can be used alone or in combination.

Preferably, the reaction is conducted by adding dropwise 2 to 2.5 molar equivalents of trifluoroacetic anhydride to the compound in dehydrated dichloromethane or tetrahydrofuran in the presence of 4 to 5 molar equivalents of a tertiary amine selected from triethylamine, diisopropylethylamine, and tributylamine at a temperature of −20 to +10° C. and treating the mixture with water at room temperature.

More preferably, the reaction is conducted by adding dropwise 2 molar equivalents of trifluoroacetic anhydride to the compound in dehydrated tetrahydrofuran in the presence of 4 molar equivalents of triethylamine at a temperature of −10 to 0° C. and subsequently treating the mixture with water at room temperature.

The compound represented by formula (C) prepared in the second step can be easily isolated by employing, after completion of the reaction, typical work-up procedure means generally used in the organic chemistry, such as extraction, washing, drying, solvent concentration, and solvent exchange, and used in the next step, or can be used in the next step without being purified after the post-treatment.

Synthesis of Compound of Formula (D) from Compound of Formula (C)

The above-obtained compound of formula (C) is reacted with a hydroxyl group activating agent and then with benzyloxyamine in the presence of a base to obtain (2S,5R)-tert-butyl 5-(benzyloxyamino)-1-(2,2,2-trifluoroacetyl)piperidine-2-carboxylate represented by formula (D):

[Chemical formula 23]

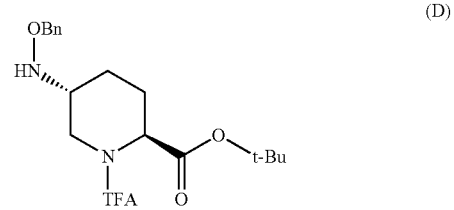

(D)

wherein, in formula (D) above, TFA represents a 2,2,2-trifluoroacetyl group, t-Bu represents a tert-butyl group, and OBn represents a benzyloxy group.

More specifically, the reaction can be conducted by dissolving the compound of formula (C) in an appropriate solvent and cooling the resultant solution, and adding, e.g., dropwise a hydroxyl group activating agent to the solution in the presence of a base and subsequently adding benzyloxyamine and a base to carry out a reaction.

The base to be present in the reaction solution can be selected from organic bases, such as triethylamine, diisopropylethylamine, tributylamine, 1,8-diazabicyclo[5.4.0]undec-7-ene, pyridine, 2-picoline, and 2,6-lutidine, and is used in an amount in the range of from 2 to 3 molar equivalents relative to the compound represented by formula (C).

The hydroxyl group activating agent can be selected from trifluoromethanesulfonyl chloride and trifluoromethanesulfonic anhydride, and is used in an amount in the range of from 1 to 1.5 molar equivalent relative to the compound represented by formula (C). The reaction is conducted at a temperature in the range of from −50 to +30° C.

Benzyloxyamine is used in an amount in the range of from 2 to 3 molar equivalents relative to the compound represented by formula (C).

The solvent used in the reaction can be selected from dichloromethane, 1,2-dichloroethane, toluene, ethyl acetate, butyl acetate, tetrahydrofuran, 1,4-dioxane, acetonitrile, N,N-dimethylformamide, and N,N-dimethylacetamide.

Preferably, the reaction is conducted by adding dropwise 1.0 to 1.2 molar equivalent of trifluoromethanesulfonic anhydride to the compound in dehydrated acetonitrile or tetrahydrofuran in the presence of 1.0 to 1.5 molar equivalent of an aromatic amine selected from pyridine, 2-picoline, and 2,6-lutidine at a temperature of −40 to −20° C. and stirring the resultant mixture at the same temperature until the compound represented by formula (C) disappears, and then adding 2 to 3 molar equivalents of benzyloxyamine and 1.0 to 1.5 molar equivalent of 2,6-lutidine to carry out a reaction at −5 to +15° C. for 2 to 3 days.

More preferably, the reaction is conducted by adding dropwise 1.05 molar equivalent of trifluoromethanesulfonic anhydride to the compound in dehydrated acetonitrile in the presence of 1.1 molar equivalent of 2,6-lutidine at a temperature of −35 to −25° C. and stirring the resultant mixture at the same temperature until the compound represented by formula (C) disappears, and then adding 2 molar equivalents of benzyloxyamine and 1.1 molar equivalent of 2,6-lutidine to carry out a reaction at a temperature of 0 to 10° C. for 2 to 3 days.

The compound represented by formula (D) prepared in the third step can be easily isolated by employing, after completion of the reaction, typical work-up procedure means generally used in the organic chemistry, such as extraction, washing, drying, solvent concentration, and solvent exchange, and used in the next step, or can be used in the next step without being purified after the post-treatment.

Synthesis of Compound of Formula (E) from Compound of Formula (D)

The above-obtained compound of formula (D) is subjected to removal of the trifluoroacetyl group in the presence of an inorganic base to obtain optically active (2S,5R)-tert-butyl 5-(benzyloxyamino)piperidine-2-carboxylate represented by formula (E):

[Chemical formula 24]

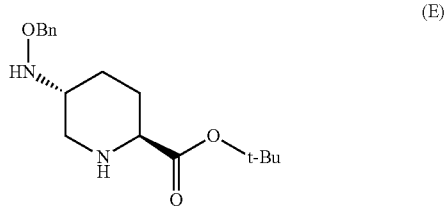

(E)

wherein, in formula (E) above, t-Bu represents a tert-butyl group, and OBn represents a benzyloxy group.

More specifically, the removal of the trifluoroacetyl group from the compound represented by formula (D) can be conducted by dissolving the compound of formula (D) in an appropriate solvent and subjecting it to solvolysis in the presence of an inorganic base.

The inorganic base can be selected from inorganic bases, such as sodium hydroxide, potassium hydroxide, lithium hydroxide, cesium hydroxide, sodium carbonate, potassium carbonate, and cesium carbonate, and is used in an amount in the range of from 1 to 3 molar equivalents relative to the compound represented by formula (D).

The solvent used in the reaction can be selected from water, methanol, ethanol, tetrahydrofuran, and 1,4-dioxane, and these solvents can be used alone or in combination. The reaction temperature is preferably 30° C. or lower.

Preferably, hydrolysis is performed using 1.5 to 2.5 molar equivalents of an inorganic base selected from sodium hydroxide, potassium hydroxide, lithium hydroxide, and cesium hydroxide in water-containing dioxane or tetrahydrofuran at 0° C. to room temperature.

More preferably, hydrolysis is performed using 2 molar equivalents of sodium hydroxide in water-containing dioxane at a temperature of 0 to 30° C.

The compound represented by formula (E) prepared in the fourth step can be easily isolated, for example, as a free base by employing, after completion of the reaction, typical work-up procedure means generally used in the organic chemistry, such as neutralization of the excess base, extraction, washing, drying, solvent concentration, solvent exchange, salt formation, and crystallization, and used in the next step, or can be used in the next step without being purified after the post-treatment.

Synthesis of Compound of Formula (F1) from Compound of Formula (E)

(5-1) Synthesis of Compound of Formula (F1) from Compound of Formula (E)

The compound represented by formula (E) is reacted with a phosgene equivalent in the presence of a base to carry out intramolecular urea formation, thus obtaining (2S,5R)-tert-butyl 6-(benzyloxy)-7-oxo-1,6-diazabicyclo[3.2.1]octane-2-carboxylate represented by formula (F1):

[Chemical formula 25]

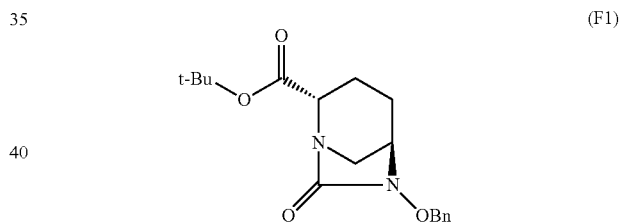

wherein, in formula (F1) above, t-Bu represents a tert-butyl group, and OBn represents a benzyloxy group.

The base used in the reaction can be selected from triethylamine, diisopropylethylamine, tributylamine, 1,8-diazabicyclo[5.4.0]undec-7-ene, pyridine, 2-picoline, 2,6-lutidine, and 4-dimethylaminopyridine, and can be preferably selected from a tertiary amine selected from triethylamine, diisopropylethylamine, and tributylamine, and an organic base, e.g., an aromatic amine, such as 4-dimethylaminopyridine, and is used in an amount in the range of from 2 to 4 molar equivalents relative to the compound represented by formula (E). When 4-dimethylaminopyridine is used as a base, it is used in an amount in the range of from 0.01 to 2 molar equivalents relative to the compound represented by formula (E).

The phosgene equivalent can be selected from phosgene, diphosgene, and triphosgene, preferably from phosgene and diphosgene, and is used in an amount in the range of from 0.5 to 2 molar equivalents relative to the compound represented by formula (E).

The solvent used in the reaction can be selected from, e.g., dichloromethane, 1,2-dichloroethane, toluene, ethyl acetate, butyl acetate, tetrahydrofuran, 1,4-dioxane, acetonitrile, N,N-dimethylformamide, and N,N-dimethylacetamide.

The reaction is conducted at a reaction concentration in the range of from 0.01 to 0.1 M. The reaction is conducted at a reaction temperature in the range of from −20 to +30° C.

Preferably, the reaction is conducted by adding to the compound in dehydrated acetonitrile or tetrahydrofuran at a concentration of from 0.01 to 0.1 M at −5 to 30° C. 2 to 3 molar equivalents of a tertiary amine selected from triethylamine, diisopropylethylamine, and tributylamine or 0.05 to 1.5 molar equivalent of 4-dimethylaminopyridine and 0.5 to 1.0 molar equivalent of diphosgene or 1.0 to 2.0 molar equivalents of phosgene and stirring the resultant mixture at room temperature.

More preferably, the reaction is conducted by adding to the compound in dehydrated acetonitrile at a concentration of from 0.025 to 0.05 M at −5 to +25° C. 2.6 to 2.8 molar equivalents of triethylamine or 0.1 to 1.0 molar equivalent of 4-dimethylaminopyridine and 0.6 to 0.7 molar equivalent of diphosgene or 1.2 to 1.4 molar equivalent of phosgene and stirring the resultant mixture at room temperature.

The compound represented by formula (F1) prepared in 5-1 step can be easily isolated by employing, after completion of the reaction, typical work-up procedure means generally used in the organic chemistry, such as neutralization of the excess base, solvent concentration, extraction, washing, drying, solvent concentration, solvent exchange, and crystallization.

(5-2) Synthesis of Compound of Formula (F1-1a) from Compound of Formula (F1)

The tert-butyl ester of the above-obtained compound of formula (F1) at the 2-position is cleaved using an acid or a metal salt, and subsequently cyclohexylamine is added thereto to obtain (2S,5R)-6-(benzyloxy)-7-oxo-1,6-diazabicyclo[3.2.1]octane-2-carboxylic acid cyclohexylamine salt represented by formula (F1-1a):

[Chemical formula 26]

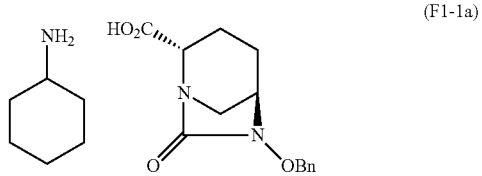

(F1-1a)

wherein, in formula (F1-1a) above, OBn represents a benzyloxy group.

The cleavage of the tert-butyl ester of the compound represented by formula (F1) using an acid or a metal salt is conducted by dissolving the compound of formula (F1) in an appropriate solvent and treating the resultant solution with an acid or a metal salt.

The acid used in the reaction can be selected from inorganic acids, such as hydrochloric acid, hydrobromic acid, sulfuric acid, phosphoric acid, and nitric acid, and organic acids, such as formic acid, acetic acid, trifluoroacetic acid, tetrafluoroboric acid, methanesulfonic acid, para-toluenesulfonic acid, and trifluoromethanesulfonic acid. The acid can be preferably selected from trifluoroacetic acid, formic acid, methanesulfonic acid, p-toluenesulfonic acid, hydrochloric acid, and sulfuric acid, and is used in an amount in the range of from 1 molar equivalent relative to the compound represented by formula (F1) to the amount of the solvent.

The metal salt used in the reaction can be selected from lithium iodide, magnesium iodide, zinc bromide, cerium chloride, titanium tetrachloride, boron trifluoride, aluminum chloride, and aluminum bromide, and is used in an amount in the range of from 1 to 6 molar equivalents relative to the compound represented by formula (F1).

The solvent used in the reaction can be selected from water, methanol, ethanol, isopropanol, ethyl acetate, butyl acetate, 1,4-dioxane, dichloromethane, 1,2-dichloroethane, and toluene, and these solvents can be used alone or in combination.

The reaction is conducted at a temperature in the range of from −25 to +25° C.

Preferably, the compound is stirred in formic acid, or in dichloromethane with 2 to 3 molar equivalents of sulfuric acid, or in trifluoroacetic acid/dichloromethane (1/1) at 0 to +25° C.

More preferably, the compound is stirred in trifluoroacetic acid/dichloromethane (1/1) at 0 to +25° C.

Then, the formation of a salt with cyclohexylamine can be conducted by performing, after completion of the above reaction, if necessary, solvent concentration, extraction, washing, drying, solvent concentration, and solvent exchange, and then adding cyclohexylamine to the resultant product in an appropriate solvent.

The equivalent of the added cyclohexylamine is selected from 1 to 4 molar equivalent relative to the compound of formula (F1).

This step is a salt formation step for synthesis of the compound of formula (F1-1) wherein M is cyclohexylammonium, but when obtaining the compound of formula (F) wherein M is an inorganic cation or organic cation other than cyclohexylammonium, the base used in the salt formation can be selected from amines, such as trimethylamine, triethylamine, cyclohexylamine, and dicyclohexylamine; organic ammonium salts, such as tetramethylammonium hydroxide, tetraethylammonium hydroxide, tetrabutylammonium hydroxide, and triethylbenzylammonium hydroxide; and salts of 2-ethylhexanoic acid with an alkali or alkaline earth metal, such as sodium, potassium, lithium, or calcium. The equivalent of the added base is selected from 1 to 5 molar equivalent relative to the compound of formula (F1).

In any of the case where M is cyclohexylammonium and the case where M is an inorganic cation or organic cation other than cyclohexylammonium, the solvent used in the salt formation can be selected from methanol, ethanol, isopropanol, acetone, methyl ethyl ketone, ethyl acetate, butyl acetate, diethyl ether, diisopropyl ether, tetrahydrofuran, 1,4-dioxane, dichloromethane, 1,2-dichloroethane, toluene, and hexane, and these solvents can be used alone or in combination.

Preferably, 1 to 4 molar equivalent of cyclohexylamine relative to the compound of formula (F1) is added to the compound in ethyl acetate to form a salt, followed by crystallization.

More preferably, 1 to 3 molar equivalent of cyclohexylamine is added to the compound in ethyl acetate to form a salt, followed by crystallization.

The salt represented by formula (F1-1) prepared in 5-2 step can be easily isolated and stored by employing typical work-up procedure means generally used in the organic chemistry, such as filtration, washing, and drying, after the salt formation and crystallization, and hence is especially excellent also as an intermediate in the industrial production.

(5-3) Synthesis of Compound of Formula (F1-2) from Compound of Formula (F1-1)

The above-obtained compound of formula (F1-1) is treated with an acid to render the carboxylic acid free, obtaining (2S,5R)-6-(benzyloxy)-7-oxo-1,6-diazabicyclo [3.2.1]octane-2-carboxylic acid represented by formula (F1-2):

[Chemical formula 27]

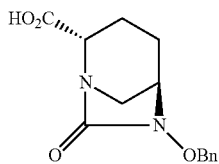

(F1-2)

wherein, in formula (F1-2) above, OBn represents a benzyloxy group.

For treating the salt of the compound represented by formula (F1-1) with an acid to render the carboxylic acid free, the compound of formula (F1-1) is dissolved in an aqueous solution of an appropriate acid and extracted with an organic solvent.

The acid used in the reaction can be selected from inorganic acids, such as hydrochloric acid, sulfuric acid, potassium hydrogensulfate, phosphoric acid, nitric acid, and sodium dihydrogenphosphate.

The organic solvent used in the extraction can be selected from organic solvents, such as dichloromethane and ethyl acetate.

Preferably, the compound of formula (F1-1) is dissolved in an aqueous solution of an inorganic acid selected from hydrochloric acid, sulfuric acid, potassium hydrogensulfate, and sodium dihydrogenphosphate and extracted with an organic solvent, such as ethyl acetate.

More preferably, the compound of formula (F1-1) is dissolved in a saturated aqueous solution of sodium dihydrogenphosphate or diluted hydrochloric acid and extracted with an organic solvent, such as ethyl acetate.

The carboxylic acid represented by formula (F1-2) prepared in 5-3 step can be isolated by employing typical work-up procedure means generally used in the organic chemistry, such as solvent extraction, concentration, solvent exchange, and crystallization, or can be used in the next step without being isolated.

(5-4) Synthesis of Compound of Formula (F1-4) from Compound of Formula (F1-2)

The above-obtained compound of formula (F1-2) is reacted with concentrated aqueous ammonia in the presence of a base and a carboxylic acid activating agent to obtain optically active (2S,5R)-6-(benzyloxy)-7-oxo-1,6-diazabicyclo[3.2.1]octane-2-carboxamide represented by formula (F1-4):

[Chemical formula 28]

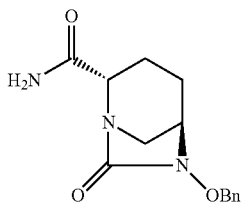

(F1-4)

wherein, in formula (F1-4) above, OBn represents a benzyloxy group.

More specifically, the compound represented by formula (F1-2) is reacted with a carboxylic acid activating agent and concentrated aqueous ammonia in an appropriate solvent in the presence of a base, or the active ester is isolated and then reacted with concentrated aqueous ammonia to obtain a carboxamide compound.

The base used in the reaction can be selected from inorganic bases, such as sodium hydrogencarbonate, potassium hydrogencarbonate, sodium carbonate, potassium carbonate, sodium hydroxide, and potassium hydroxide, and organic bases, such as triethylamine, diisopropylethylamine, tributylamine, 1,8-diazabicyclo[5.4.0]undec-7-ene, pyridine, 2-picoline, 2,6-lutidine, and 4-dimethylaminopyridine, and can be preferably selected from triethylamine, diisopropylethylamine, and tributylamine, and can be used in an amount in the range of from 0.8 to 1.5 molar equivalent relative to the compound represented by formula (F1-2).

The carboxylic acid activating agent used in the reaction can be selected from acid chlorides, such as ethyl chloroformate, isobutyl chloroformate, pivaloyl chloride, and 2,4, 6-trichlorobenzoyl chloride, and acid anhydrides, such as isovaleric anhydride and pivalic anhydride, preferably from ethyl chloroformate, isobutyl chloroformate, and pivaloyl chloride, and is used in an amount in the range of from 0.8 to 1.5 molar equivalent relative to the compound represented by formula (F1-2).

The solvent used in the reaction can be selected from water, dichloromethane, 1,2-dichloroethane, toluene, ethyl acetate, butyl acetate, tetrahydrofuran, 1,4-dioxane, acetonitrile, N,N-dimethylformamide, N,N-dimethylacetamide, and pyridine, and these solvents can be used alone or in combination.

This step can be conducted in the presence of a condensing agent. The condensing agent can be selected from a single carbodiimide, such as N,N'-dicyclohexylcarbodiimide or 1-ethyl-3-(3-dimethylaminopropyl)carbodiimide hydrochloride; and combinations of a catalyst, such as 1-hydroxybenzotriazole, N-hydroxysuccinimide, or 2-hydroxypyridine-N-oxide, and benzotriazol-1-yloxy-tris(dimethylamino)phosphonium hexafluorophosphate, 2-chloro-1-methylpyridinium iodide, or (4,6-dimethoxy-1,3,5-triazin-2-yl)-4-methylmorpholinium chloride. The condensing agent can be used in an amount in the range of from 0.8 to 1.5 molar equivalent relative to the compound represented by formula (F1-2).

Concentrated aqueous ammonia is used in an amount in the range of from 5 to 100 molar equivalents relative to the compound represented by formula (F1-2).

The reaction is conducted at a reaction temperature in the range of from −20 to +25° C.

Preferably, in this step, the compound is reacted with 1.1 molar equivalent of a mixed acid anhydride reagent selected from ethyl chloroformate, isobutyl chloroformate, and pivaloyl chloride in dehydrated dichloromethane in the presence of 1.2 molar equivalent of a tertiary amine selected from triethylamine, diisopropylethylamine, and tributylamine at −5 to +5° C. and then reacted with 5 to 50 molar equivalents of concentrated aqueous ammonia.

More preferably, the compound is reacted with 1.1 molar equivalent of isobutyl chloroformate in dichloromethane in the presence of 1.2 molar equivalent of triethylamine at −5 to +5° C. and then reacted with 5 to 20 molar equivalents of concentrated aqueous ammonia.

The carboxamide compound represented by formula (F1-4) prepared in 5-4 step can be isolated by employing typical work-up procedure means generally used in the organic chemistry, such as solvent extraction, washing, drying, solvent concentration, solvent exchange, and crystallization.

(5-5) Synthesis of Compound of Formula (F1-3a), Formula (F1-3b), Formula (F1-3c), or Formula (F1-3d) from Compound of Formula (F1-2); and Synthesis of Compound of Formula (F2-3) from Compound of Formula (F2-2)

The above-obtained compound represented by formula (F1-2) or the below-mentioned compound of formula (F2-2) is subjected to esterification of the carboxylic acid at the 2-position to obtain (2S,5R)-methyl 6-(benzyloxy)-7-oxo-1,6-diazabicyclo[3.2.1]octane-2-carboxylate represented by formula (F1-3a):

[Chemical formula 29]

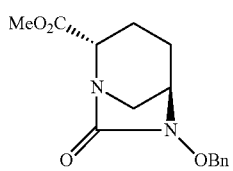

(F1-3a)

wherein, in formula (F1-3a), Me represents a methyl group, and OBn represents a benzyloxy group;

(2S,5R)-allyl 6-(benzyloxy)-7-oxo-1,6-diazabicyclo[3.2.1]octane-2-carboxylate represented by formula (F1-3b):

[Chemical formula 30]

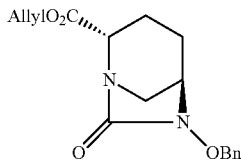

(F1-3b)

wherein, in formula (F1-3b), OBn represents a benzyloxy group;

(2S,5R)-benzyl 6-(benzyloxy)-7-oxo-1,6-diazabicyclo[3.2.1]octane-2-carboxylate represented by formula (F1-3c):

[Chemical formula 31]

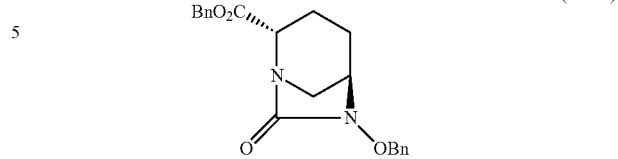

(F1-3c)

wherein, in formula (F1-3c), Bn represents a benzyl group, and OBn represents a benzyloxy group;

(2S,5R)-2,5-dioxopyrrolidin-1-yl 6-(benzyloxy)-7-oxo-1,6-diazabicyclo[3.2.1]octane-2-carboxylate represented by formula (F1-3d):

[Chemical formula 32]

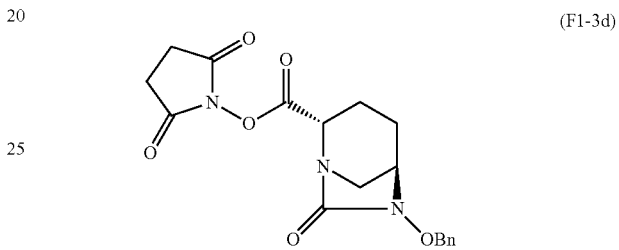

(F1-3d)

wherein, in formula (F1-3d), OBn represents a benzyloxy group; or a compound defined by formula (F2-3):

[Chemical formula 33]

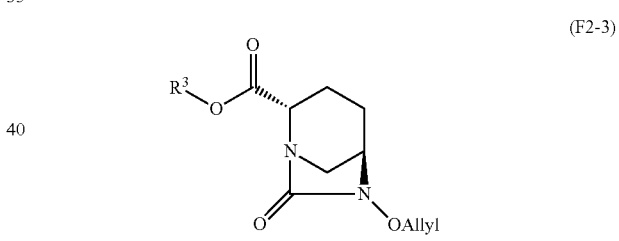

(F2-3)

wherein, in formula (F2-3), $R^3$ represents a methyl group, an allyl group, a benzyl group, or a 2,5-dioxopyrrolidin-1-yl group.

More specifically, the esterification of the compound represented by formula (F1-2) and the compound represented by formula (F2-2) can be conducted by reacting the compound with an alkyl halide, an allyl halide, or a benzyl halide in an appropriate solvent in the presence of an alkylating agent and a base; or by reacting the compound with a carboxylic acid activating agent or a dehydration condensing agent and an alcohol in the presence of a base.

The alkylating agent used in the reaction can be selected from diazoalkyls, such as diazomethane, trimethylsilyldiazomethane, and diphenyldiazomethane, and halogen compounds, such as methyl iodide, ethyl iodide, allyl chloride, allyl bromide, benzyl chloride, benzyl bromide, para-nitrobenzyl bromide, and para-methoxybenzyl bromide.

The base used in the reaction can be selected from inorganic bases, such as sodium hydrogencarbonate, potassium hydrogencarbonate, sodium carbonate, potassium carbonate, cesium carbonate, sodium hydroxide, and potassium hydroxide, and organic bases, such as triethylamine, diisopropylethylamine, tributylamine, 1,8-diazabicyclo[5.4.0]undec-7-ene, pyridine, 2-picoline, 2,6-lutidine, and 4-dimethylaminopyridine.

The carboxylic acid activating agent or condensing agent used in the reaction can be selected from a single carbodiimide, such as N,N'-dicyclohexylcarbodiimide or 1-ethyl-3-(3-dimethylaminopropyl)carbodiimide hydrochloride; combinations of a catalyst, such as 1-hydroxybenzotriazole or 2-hydroxypyridine-N-oxide, and a carboxylic acid activating agent, such as benzotriazol-1-yloxy-tris(dimethylamino) phosphonium hexafluorophosphate, 2-chloro-1-methylpyridinium iodide, or (4,6-dimethoxy-1,3,5-triazin-2-yl)-4-methylmorpholinium chloride; and mixed acid anhydride reagents comprising an acid chloride, such as ethyl chloroformate, isobutyl chloroformate, pivaloyl chloride, or 2,4,6-trichlorobenzoyl chloride, and an acid anhydride, such as isovaleric anhydride or pivalic anhydride.

The solvent used in the esterification reaction can be selected from water, dichloromethane, 1,2-dichloroethane, toluene, ethyl acetate, butyl acetate, tetrahydrofuran, 1,4-dioxane, acetonitrile, N,N-dimethylformamide, N,N-dimethylacetamide, and pyridine, and these solvents can be used alone or in combination.

The alcohol used in the reaction can be selected from methanol, allyl alcohol, benzyl alcohol, and 2,5-dioxopyrrolidin-1-ol.

In this step, when methyl esterification is conducted, it is preferred that the compound is reacted with 1 to 1.5 molar equivalent of trimethylsilyldiazomethane in a toluene-methanol mixed solvent while cooling with ice.

When allyl esterification is conducted, it is preferred that the compound is reacted with 1 to 3 molar equivalents of allyl bromide in N,N-dimethylformamide in the presence of 1 to 3 molar equivalents of sodium hydrogencarbonate at room temperature.

When benzyl esterification is conducted, it is preferred that the compound is reacted with 1.5 to 2.5 molar equivalents of benzyl alcohol in dichloromethane in the presence of 1.3 to 1.7 molar equivalent of 1-ethyl-3-(3-dimethylaminopropyl) carbodiimide hydrochloride at room temperature.

When 2,5-dioxopyrrolidin-1-yl esterification is conducted, it is preferred that the compound is reacted with isobutyl chloroformate in dichloromethane in the presence of a tertiary amine and then with N-hydroxysuccinimide while cooling with ice.

The compounds represented by formulae (F1-3a), (F1-3b), (F1-3c), and (F1-3d) prepared in 5-5 step and the compound represented by formula (F2-3c), which is a specific compound of the compound represented by formula (F2-3), can be isolated by employing, after completion of the reaction, typical work-up procedure means generally used in the organic chemistry, such as solvent extraction, separation and washing, drying, solvent concentration, and crystallization.

(5-6) Synthesis of Compound of Formula (F1-2) from Compound of Formula (F1-3a) (5-6.1 step)

The methyl ester of the above-obtained compound of formula (F1-3a) is hydrolyzed using an inorganic base to obtain a compound of formula (F1-2).

More specifically, the cleavage of the methyl ester of the compound represented by formula (F1-3a) obtained by the above-mentioned method can be conducted by dissolving the compound of formula (F1-3a) in an appropriate solvent, followed by solvolysis in the presence of an appropriate base.

The inorganic base used in the reaction can be selected from inorganic bases, such as sodium carbonate, potassium carbonate, cesium carbonate, lithium hydroxide, sodium hydroxide, potassium hydroxide, and cesium hydroxide, and is used in an amount in the range of from 1.0 to 1.5 molar equivalent relative to the compound represented by formula (F1-3a).

The solvent used in the reaction can be selected from water, methanol, ethanol, propanol, isopropanol, butanol, ether, diisopropyl ether, toluene, tetrahydrofuran, and 1,4-dioxane, and these solvents can be used alone or in combination.

The reaction is conducted at a reaction temperature in the range of from −20 to +25° C.

Preferably, the compound of formula (F1-3a) is stirred in water-tetrahydrofuran at −10 to +10° C., together with 1.0 to 1.2 equivalent of lithium hydroxide.

More preferably, the compound of formula (F1-3a) is stirred in water-tetrahydrofuran at −5 to +5° C., together with 1.0 to 1.1 equivalent of lithium hydroxide.

The carboxylic acid represented by (F1-2) prepared in 5-6.1 step can be isolated by employing, after completion of the reaction, typical work-up procedure means generally used in the organic chemistry, such as solvent concentration, acidification, solvent extraction, separation and washing, drying, solvent concentration, and salt formation, and used in the next step, or can be used in the next step without being isolated.

(5-6) Synthesis of Compound of Formula (F1-2) from Compound of Formula (F1-3b) via Compound of Formula (F1-1a) (5-6.2 step)

The above-obtained compound represented by formula (F1-3b) is reacted with a nucleophile in the presence of a catalyst to cleave the allyl ester, and subsequently cyclohexylamine is added thereto to obtain a compound of formula (F1-1a), followed by a treatment with an inorganic acid, to render the carboxylic acid of the compound free, obtaining a compound of formula (F1-2).

More specifically, the cleavage of the allyl ester of the compound represented by formula (F1-3b) can be conducted by dissolving the compound of formula (F1-3b) in an appropriate solvent and treating the resultant solution with an appropriate nucleophile in the presence of a catalyst.

The catalyst used in the reaction can be selected from palladium acetate, tetrakis(triphenylphosphine)palladium, dichlorobis(triphenylphosphine)palladium, chlorotris(triphenylphosphine)rhodium, and lithium dimethylcopper, and can be used in an amount in the range of from 0.01 to 0.1 molar equivalent relative to the compound represented by formula (F1-3b).

The nucleophile used in the reaction can be selected from sodium 2-ethylhexanoate, sodium 2-methylhexanoate, pyrrolidine, dimedone, benzyloxyamine, and sodium benzenesulfenate, and can be used in an amount in the range of from 1 to 2 molar equivalents relative to the compound represented by formula (F1-3b).

The solvent used in the reaction can be selected from water, methanol, ethanol, propanol, isopropanol, butanol, ether, diisopropyl ether, ethyl acetate, butyl acetate, dichloromethane, dichloroethane, toluene, tetrahydrofuran, 1,4-dioxane, and acetonitrile, and these solvents can be used alone or in combination.

The reaction temperature is selected from −20 to +25° C.

In this step, preferably, the compound represented by formula (F1-3b) is stirred in tetrahydrofuran, acetonitrile, or dichloromethane at room temperature, together with 1 to 2 molar equivalents of sodium 2-ethylhexanoate, pyrrolidine, or dimedone, in the presence of 0.01 to 0.05 molar equivalent of palladium acetate, dichlorobis (triphenylphosphine) palladium, or tetrakis(triphenylphosphine)palladium.

More preferably, the compound represented by formula (F1-3b) is stirred in dichloromethane at 20° C., together with 1 to 1.5 molar equivalent of sodium 2-ethylhexanoate, in the presence of 0.01 to 0.03 molar equivalent of tetrakis(triphenylphosphine)palladium.

Thus obtained compound having cleaved the allyl ester is treated with cyclohexylamine to obtain a compound of formula (F1-1a), and then the compound is treated with an inorganic acid selected from hydrochloric acid, sulfuric acid, potassium hydrogensulfate, and sodium dihydrogenphosphate to render the carboxylic acid free, obtaining a compound of formula (F1-2).

The carboxylic acid represented by formula (F1-2) prepared in 5-6.2 step can be isolated by employing, after completion of the reaction, typical work-up procedure means generally used in the organic chemistry, such as solvent concentration, acidification, solvent extraction, separation and washing, drying, solvent concentration, and salt formation, and used in the next step, or can be used in the next step without being isolated.

(5-7) Synthesis of Compound of Formula (F1-4) from Compound of Formula (F1-3d)

The above-obtained compound represented by formula (F1-3d) is reacted with aqueous ammonia to obtain a compound represented by formula (F1-4).

More specifically, the reaction can be conducted by dissolving the compound represented by formula (F1-3d) in an appropriate solvent and treating the resultant solution with concentrated aqueous ammonia.

Concentrated aqueous ammonia is used in an amount in the range of from 5 to 100 molar equivalents relative to the compound represented by formula (F1-3d).

The solvent used in the reaction can be selected from water, dichloromethane, 1,2-dichloroethane, toluene, ethyl acetate, butyl acetate, tetrahydrofuran, 1,4-dioxane, acetonitrile, N,N-dimethylformamide, and N,N-dimethylacetamide, and these solvents can be used alone or in combination.

The reaction is conducted at a reaction temperature in the range of from −20 to +25° C.

In this step, preferably, the compound represented by formula (F1-3d) is reacted with 5 to 50 molar equivalents of concentrated aqueous ammonia in dehydrated dichloromethane at −5 to +5° C.

More preferably, the compound represented by formula (F1-3d) is reacted with 5 to 20 molar equivalents of concentrated aqueous ammonia in dichloromethane at −5 to +5° C.

The carboxamide compound represented by formula (F1-4) prepared in 5-7 step can be isolated by employing typical work-up procedure means generally used in the organic chemistry, such as solvent extraction, washing, drying, solvent concentration, solvent exchange, and crystallization.

(5-8) Synthesis of Compound of Formula (F2) from Compound of Formula (F1)

The benzyl group of the above-obtained compound represented by formula (F1) is removed by a catalytic hydrogenation reaction, and subsequently the resultant compound is reacted with an allylation agent in the presence of a base to obtain (2S,5R)-tert-butyl 6-(allyloxy)-7-oxo-1,6-diazabicyclo[3.2.1]octane-2-carboxylate represented by formula (F2):

[Chemical formula 34]

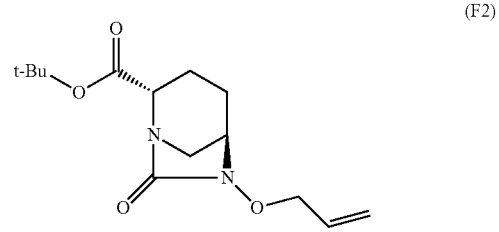

wherein, in formula (F2) above, t-Bu represents a tert-butyl group.

More specifically, the conversion of the benzyl group of the compound represented by formula (F1) to an allyl group can be conducted by dissolving the compound of formula (F1) in an appropriate solvent and subjecting to a hydrogenation reaction using a catalyst and then an allylation reaction in the presence of a base.

The catalyst used in the reaction can be selected from arbitrary hydrogenation catalysts, and Raney nickel, platinum oxide, palladium oxide, palladium black, or palladium-carbon can be preferably used.

The hydrogen pressure can be from atmospheric pressure to 0.5 MPa.

The solvent used in the hydrogenation reaction can be selected from water, methanol, ethanol, propanol, isopropanol, butanol, ether, diisopropyl ether, ethyl acetate, butyl acetate, toluene, tetrahydrofuran, and 1,4-dioxane, and these solvents can be used alone or in combination.

The step for hydrogenation is preferably conducted in methanol or ethanol using a catalyst selected from platinum oxide, palladium oxide, palladium black, and palladium-carbon.

More preferably, the step is conducted in ethanol using palladium-carbon as a catalyst.

The 6-hydroxy compound having removed the benzyl group obtained by the above hydrogenation step can be used in the next step without being isolated by employing, after completion of the reaction, typical work-up procedure means generally used in the organic chemistry, such as filtration for catalyst, solvent concentration, and solvent exchange.

The base used in the allylation reaction can be selected from inorganic bases, such as sodium hydrogencarbonate, potassium hydrogencarbonate, sodium carbonate, potassium carbonate, cesium carbonate, sodium hydroxide, and potassium hydroxide, and organic bases, such as triethylamine, diisopropylethylamine, tributylamine, 1,8-diazabicyclo[5.4.0]undec-7-ene, pyridine, 2-picoline, 2,6-lutidine, and 4-dimethylaminopyridine, and can be used in an amount in the range of from 1.0 to 3 molar equivalents relative to the compound represented by formula (F1).

The allylation agent used in the allylation reaction can be selected from allyl chloride and allyl bromide, and can be used in an amount in the range of from 1.0 to 3 molar equivalents relative to the compound represented by formula (F1).

The solvent used in the allylation reaction can be selected from dichloromethane, 1,2-dichloroethane, toluene, ethyl acetate, butyl acetate, tetrahydrofuran, 1,4-dioxane, acetonitrile, N,N-dimethylformamide, and N,N-dimethylacetamide.

The reaction is conducted at a reaction temperature of 0 to +25° C.

In the step for allylation reaction, preferably, the compound is stirred in dehydrated acetonitrile, N,N-dimethylformamide, or N,N-dimethylacetamide at room temperature, together with 1 to 2 molar equivalents of allyl bromide, in the presence of 1 to 2 molar equivalents of an inorganic base selected from anhydrous sodium carbonate, potassium carbonate, and cesium carbonate.

More preferably, the compound is stirred in dehydrated acetonitrile at room temperature, together with 1 to 2 molar equivalents of allyl bromide, in the presence of 1 molar equivalent of anhydrous potassium carbonate.

The compound represented by formula (F2) prepared in 5-8 step can be isolated by employing, after completion of the reaction, typical treatment means generally used in the organic chemistry, such as solvent concentration, solvent exchange, separation and washing, drying, and solvent concentration.

(5-9) Synthesis of Compound of Formula (F2-1a) from Compound of Formula (F2)

The tert-butyl ester of the above-obtained compound of formula (F2) at the 2-position is cleaved using an acid, and subsequently cyclohexylamine is added thereto to obtain (2S,5R)-6-(allyloxy)-7-oxo-1,6-diazabicyclo[3.2.1]octane-2-carboxylic acid cyclohexylamine salt represented by formula (F2-1a):

[Chemical formula 35]

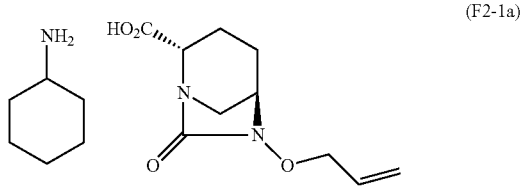

(F2-1a)

The cleavage of the tert-butyl ester of the compound represented by formula (F2) using an acid is conducted by dissolving the compound of formula (F2) in an appropriate solvent and performing the same process as in 5-2 step. With respect to the acid, trifluoroacetic acid, methanesulfonic acid, p-toluenesulfonic acid, hydrochloric acid, or sulfuric acid can be preferably used, and after the cleavage of the tert-butyl ester using the acid, a treatment with cyclohexylamine results in a cyclohexylamine salt.

The salt represented by formula (F2-1a) prepared in 5-9 step can be easily isolated and stored by employing typical work-up procedure means generally used in the organic chemistry, such as filtration, washing, and drying, after the salt formation and crystallization, and hence is especially excellent also as an intermediate in the industrial production.

(5-10) Synthesis of Compound of Formula (F2-2) from Compound of Formula (F2-1a)

The above-obtained compound of formula (F2-1a) is treated with an acid to render the carboxylic acid free, obtaining (2S,5R)-6-(allyloxy)-7-oxo-1,6-diazabicyclo[3.2.1]octane-2-carboxylic acid represented by formula (F2-2):

[Chemical formula 36]

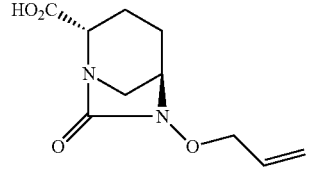

(F2-2)

For treating the salt represented by formula (F2-1a) with an acid to render the carboxylic acid free, the compound of formula (F2-1a) is dissolved in an aqueous solution of an appropriate acid and subjected to the same process as in 5-3 step. With respect to the acid, an inorganic acid, such as hydrochloric acid, sulfuric acid, potassium hydrogensulfate, or sodium dihydrogenphosphate, can be used.

The carboxylic acid represented by formula (F2-2) prepared in 5-10 step can be isolated by employing typical work-up procedure means generally used in the organic chemistry, such as solvent extraction, concentration, and solvent exchange, and used in the next step, or can be used in the next step without being isolated.

(5-5) Synthesis of Compound of Formula (F2-3c) from Compound of Formula (F2-2)

The carboxylic acid of the above-obtained compound represented by formula (F2-2) at the 2-position is reacted with benzyl alcohol in the presence of a dehydration condensing agent to obtain (2S,5R)-benzyl 6-(allyloxy)-7-oxo-1,6-diazabicyclo[3.2.1]octane-2-carboxylate which is a specific compound of the compound represented by formula (F2-3), and which is represented by formula (F2-3c):

[Chemical formula 37]

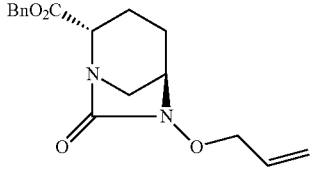

(F2-3c)

wherein, in formula (F2-3c) above, Bn represents a benzyl group.

The compounds represented by formulae (F1), (F1-3a), and (F1-3b) below obtained in the above steps can be crystallized from, for example, ethyl acetate and hexane solution. The compound represented by formula (F1-1a) can be crystallized from, for example, ethyl acetate-ether. Further, the compound represented by formula (F1-2) can be crystallized from, for example, ethyl acetate-hexane. Furthermore, the compound represented by formula (F1-4) can be crystallized from, for example, chloroform and hexane solution.

[Chemical formula 38]

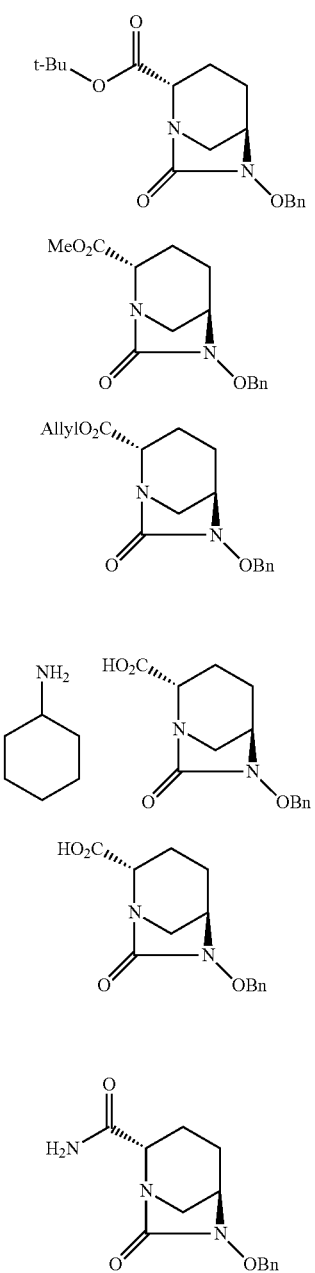

In the above formulae, t-Bu represents a tert-butyl group, OBn represents a benzyloxy group, and Me represents a methyl group.

With respect to the compounds represented by formulae (F1), (F1-3a), (F1-3b), (F1-1a), (F1-2) and (F1-4) which can be prepared as mentioned above, the observation under a polarizing microscope and the powder X-ray diffractometry have confirmed that each of the compounds can be obtained as a crystal, and especially in the powder X-ray diffractometry, each compound is identified by the characteristics peaks. The peak patterns of the compounds are shown in Tables 1 to 6 below.

TABLE 1

Powder X-ray data
Powder X-ray diffraction of compound (F1)

Peak position

| 2θ (Cukα) | Lattice spacing (d) Å | Relative intensity I/I0 |
|---|---|---|
| 7.64 | 11.56 | 13 |
| 8.06 | 10.96 | 67 |
| 13.50 | 6.55 | 46 |
| 14.74 | 6.00 | 15 |
| 15.30 | 5.79 | 11 |
| 15.92 | 5.56 | 44 |
| 16.18 | 5.47 | 58 |
| 16.86 | 5.25 | 64 |
| 18.10 | 4.90 | 46 |
| 20.38 | 4.35 | 18 |
| 20.96 | 4.23 | 100 |
| 23.04 | 3.86 | 10 |

TABLE 2

Powder X-ray data
Powder X-ray diffraction of compound (F1-3a)

Peak position

| 2θ (Cukα) | Lattice spacing (d) Å | Relative intensity I/I0 |
|---|---|---|
| 8.50 | 10.39 | 92 |
| 15.10 | 5.86 | 9 |
| 15.56 | 5.69 | 66 |
| 16.60 | 5.34 | 11 |
| 18.42 | 4.81 | 28 |
| 19.98 | 4.44 | 100 |
| 22.30 | 3.98 | 9 |
| 23.50 | 3.78 | 66 |
| 28.64 | 3.11 | 13 |
| 29.44 | 3.03 | 19 |
| 30.52 | 2.93 | 13 |
| 32.28 | 2.77 | 11 |

TABLE 3

Powder X-ray data
Powder X-ray diffraction of compound (F1-3b)

Peak position

| 2θ (Cukα) | Lattice spacing (d) Å | Relative intensity I/I0 |
|---|---|---|
| 6.00 | 14.72 | 100 |
| 18.06 | 4.91 | 26 |
| 19.88 | 4.46 | 10 |
| 20.94 | 4.24 | 10 |
| 24.22 | 3.67 | 12 |

TABLE 4

Powder X-ray data
Powder X-ray diffraction of compound (F1-1a)

Peak position

| 2θ (Cukα) | Lattice spacing (d) Å | Relative intensity I/I0 |
|---|---|---|
| 8.88 | 9.95 | 46 |
| 10.46 | 8.45 | 9 |
| 14.14 | 6.26 | 14 |

TABLE 4-continued

Powder X-ray data
Powder X-ray diffraction of compound (F1-1a)

| 2θ (Cuka) | Lattice spacing (d) Å | Relative intensity I/I0 |
|---|---|---|
| _____ Peak position _____ | | |
| 15.08 | 5.87 | 17 |
| 16.04 | 5.52 | 100 |
| 16.98 | 5.22 | 71 |
| 17.38 | 5.10 | 17 |
| 17.88 | 4.96 | 26 |
| 18.74 | 4.73 | 57 |
| 19.52 | 4.54 | 22 |
| 21.36 | 4.16 | 13 |
| 22.60 | 3.93 | 68 |
| 25.08 | 3.55 | 12 |

TABLE 5

Powder X-ray data
Powder X-ray diffraction of compound (F1-2)

| 2θ (Cuka) | Lattice spacing (d) Å | Relative intensity I/I0 |
|---|---|---|
| _____ Peak position _____ | | |
| 10.80 | 8.19 | 10 |
| 12.38 | 7.14 | 14 |
| 13.32 | 6.64 | 11 |
| 14.06 | 6.29 | 81 |
| 15.82 | 5.60 | 33 |
| 17.02 | 5.21 | 92 |
| 18.04 | 4.91 | 12 |
| 19.28 | 4.60 | 37 |
| 21.06 | 4.21 | 100 |
| 24.08 | 3.69 | 42 |
| 25.80 | 3.45 | 16 |
| 28.52 | 3.13 | 33 |

TABLE 6

Powder X-ray data
Powder X-ray diffraction of compound (F1-4)

| 2θ (Cuka) | Lattice spacing (d) Å | Relative intensity I/I0 |
|---|---|---|
| _____ Peak position _____ | | |
| 6.76 | 13.06 | 100 |
| 13.58 | 6.52 | 23 |
| 17.24 | 5.14 | 48 |
| 18.70 | 4.74 | 34 |
| 19.16 | 4.63 | 13 |
| 20.46 | 4.34 | 45 |
| 23.08 | 3.85 | 17 |
| 23.92 | 3.72 | 8 |

The compound defined by formula (F) of the present invention can be used as a preparation intermediate for obtaining a compound represented by formula (H) below. The compound represented by formula (H) below and the antipode thereof were prepared from the compound represented by formula (F) of the present invention as a starting material, and compared in respect of the biological activity.

[Chemical formula 39]

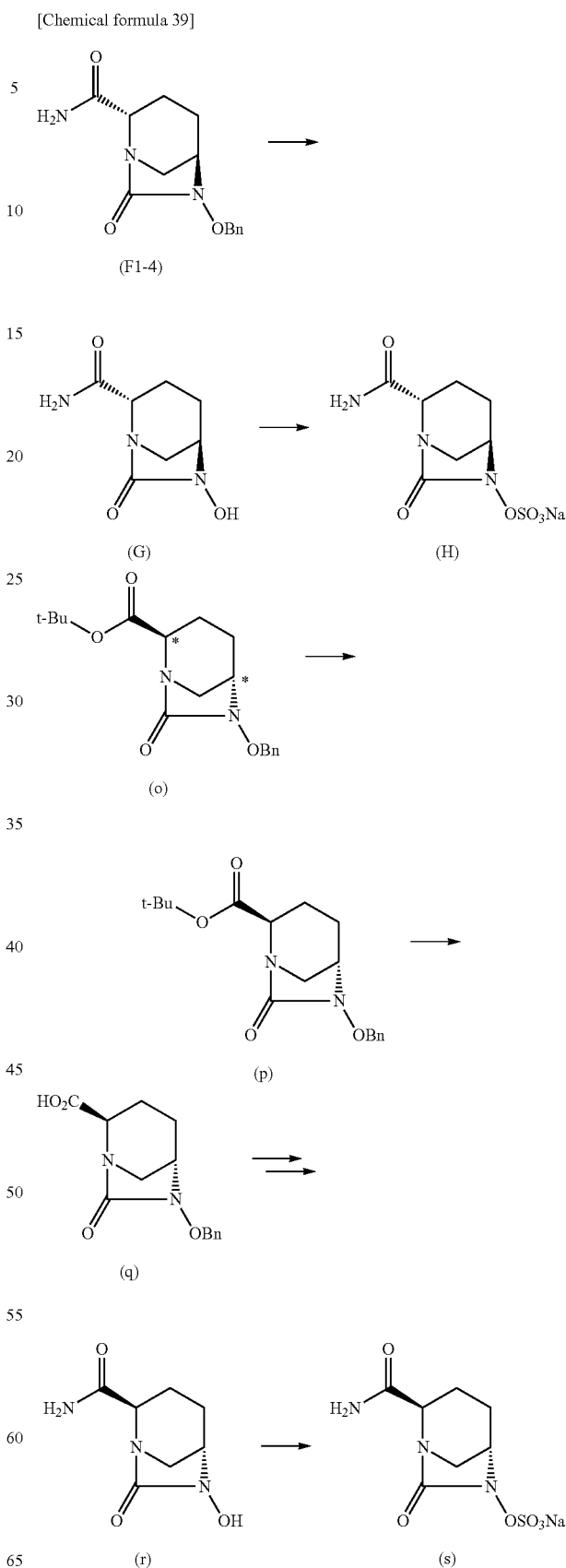

In the above chemical reaction scheme, t-Bu represents a tert-butyl group, and OBn represents a benzyloxy group.

The compound represented by formula (H) was prepared from a compound represented by formula (F1-4) among the compounds represented by formula (F) obtained by the method of the present invention. Further, racemic (2R/S,5S/R)-tert-butyl 6-(benzyloxy)-1,6-diazabicyclo[3.2.1]octane-2-carboxylate represented by formula (o) was prepared, and subjected to optical resolution using a chiral column to obtain the antipode represented by formula (p), thus preparing (2R,5S)-1,6-diazabicyclo[3.2.1]octane-2-carboxamide, 7-oxo-6-(sulfoxy)-mono sodium salt represented by formula (s) through the antipode.

With respect to each of the obtained compounds of formulae (H) and (s), the β-lactamase enzyme inhibitory activity and the effect of the each compound in combination with an antibiotic were evaluated. As a result, it was found that the compound represented by formula (H) exhibited the activities, but the compound represented by formula (s) exhibited no activity. The results have confirmed that the compound of formula (F) which can be obtained by the process of the present invention is an enantiomer especially useful as a raw material for drug and an intermediate therefor.

TABLE 7

Biological activity of formulae (H) and (s)

| Compound | Optical rotation [α]Error! | IC$_{50}$ μM | MIC μg/mL |
|---|---|---|---|
| H | −37.1° | 0.65 | 4 |
| s | +38.1° | >30 | 64 |
| TAZ | — | 0.95 | 64 |

In Table 7 above, TAZ represents Tazobactam, IC$_{50}$ indicates an enzyme inhibitory activity against AmpC, and MIC indicates an antimicrobial activity of Piperacillin (PIPC) when used in combination with 4 μg/mL of the compound.

In this case, the antipode represented by formula (p) is obtained from the racemic compound by optical resolution, but the antipodes represented by formulae (r) and (s) cannot be separated from the corresponding racemic compounds using a chiral column of a normal phase or a reversed phase. This also has confirmed that the racemic compounds represented by formula (o) having a tert-butyl ester exhibits excellent properties as an intermediate such that a special solvent is not necessary as a mobile phase, that the separation from its antipode is easy, and that it is unlikely to decompose during the concentration of the active fraction.

Further, the compounds represented by formulae (F1-2) and (F1-4) can be used also as an important intermediate for the preparation of an optically active compound for the β-lactamase inhibitor having a diazabicyclooctane skeleton shown in patent documents 1 to 6, or for the research of a more highly effective novel β-lactamase inhibitor and for the pharmaceutical development.

[Chemical formula 40]

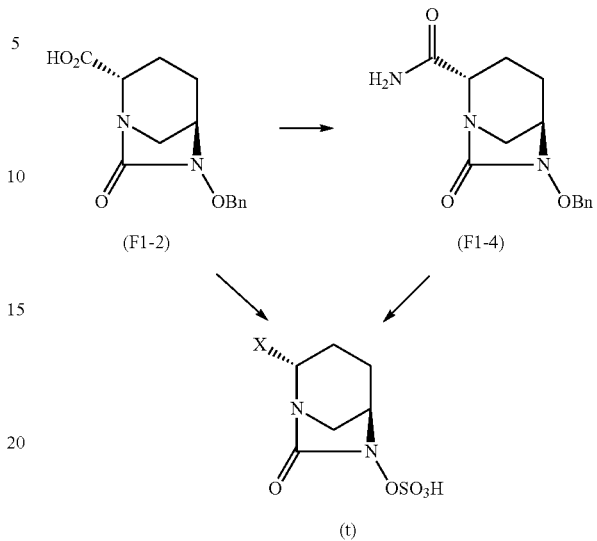

(t)

In the above chemical reaction scheme, OBn represents a benzyloxy group, and X represents an active substituent.

The biological activity of the above-mentioned compounds represented by formulae (H) and (s) can be measured as follows. Specifically, an enzyme inhibitory activity (IC$_{50}$ value) against AmpC enzyme which is a class C β-lactamase was determined using nitrocephin as a substrate to check whether or not the compounds had the inhibitory activity and compare the activities of them. Further, using constitutive AmpC producing *Pseudomonas aeruginosa*, a combined antimicrobial activity (MIC) was measured when using Piperacillin (PIPC) as an antibiotic and the compound of formula (H) or (s) in combination to check whether or not the antimicrobial activity of PIPC could be restored.

Thus, in the present invention, there is also provided use of the following specific compounds represented by formula (F) for the manufacture of a medicament for treatment of an infectious disease wherein the medicament comprises a β-lactamase inhibitor containing a (2S,5R)-7-oxo-1,6-diazabicyclo[3.2.1]octane-2-carboxylic acid derivative:

(2S,5R)-tert-Butyl 6-(benzyloxy)-7-oxo-1,6-diazabicyclo[3.2.1]octane-2-carboxylate;

(2S,5R)-Methyl 6-(benzyloxy)-7-oxo-1,6-diazabicyclo[3.2.1]octane-2-carboxylate;

(2S,5R)-Allyl 6-(benzyloxy)-7-oxo-1,6-diazabicyclo[3.2.1]octane-2-carboxylate;

(2S,5R)-Benzyl 6-(benzyloxy)-7-oxo-1,6-diazabicyclo[3.2.1]octane-2-carboxylate;

(2S,5R)-6-(Benzyloxy)-7-oxo-1,6-diazabicyclo[3.2.1]octane-2-carboxylic acid cyclohexyl ammonium salt;

(2S,5R)-6-(Benzyloxy)-7-oxo-1,6-diazabicyclo[3.2.1]octane-2-carboxylic acid;

(2S,5R)-6-(Benzyloxy)-7-oxo-1,6-diazabicyclo[3.2.1]octane-2-carboxamide; and (2S,5R)-tert-Butyl 5-(benzyloxyamino)piperidine-2-carboxylate.

EXAMPLES

Hereinafter, the present invention will be illustrated in more detail by examples, but the present invention is not intended to be limited by examples, with various modifications being possible.

Reference Example 1

(2S,5S)-1-Benzyl 2-tert-butyl 5-hydroxypiperidine-1,2-dicarboxylate (A)

Step 1: (S)-1-Benzyl 2-tert-butyl 5-oxopyrrolidine-1,2-dicarboxylate

[Chemical formula 41]

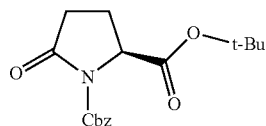

100 g of (S)-1-(benzyloxycarbonyl)-5-oxopyrrolidine-2-carboxylic acid was dissolved in dehydrated dichloromethane (2 L), and under ice cooling, concentrated sulfuric acid (10 mL) and 213 g of isobutene were added, followed by stirring overnight at +20° C. or less. The reaction mixture was added to cold aqueous sodium carbonate solution while paying attention to effervescence, followed by liquid separation of the organic phase, washing with saturated brine and drying over anhydrous magnesium sulfate, and the solvent was concentrated under reduced pressure. The residue was subjected to silica gel column chromatography (hexane/ethyl acetate=7/3), and crystallized with hexane/ethyl acetate to afford 80 g of the title compound as a colorless crystalline powder (yield 67%). Enantiomeric excess: 99.9% ee or more (CHIRALPAK AD-H, 4.6×150 mm, UV 210 nm, hexane/ethanol=2/1, flow rate 1 mL/min., retention time 4.2 min.).

$[\alpha]^{20}_D$ –43.3°(c 0.52 in CHCl$_3$), according to Non-Patent Document 4 –41.8°(c 6.71, CHCl$_3$); $^1$H NMR (400 MHz, CDCl$_3$, δ): 1.39 (s, 9H), 2.04 (m, 1H), 2.32 (m, 1H), 2.51 (ddd, J=17.6, 9.5, 3.2 Hz, 1H), 2.62 (ddd, J=17.6, 10.5, 9.5 Hz, 1H), 4.55 (dd, J=9.5, 2.7 Hz, 1H), 5.25 (d, J=12.2 Hz, 1H), 5.30 (d, J=12.2 Hz, 1H), 7.26-7.41 (m, 5H); MS m/z: 320 (M+1).

Step 2: (S)-tert-Butyl 2-(benzyloxycarbonylamino)-5-oxo-6-dimethylsulfoxonium hexanoate

[Chemical formula 42]

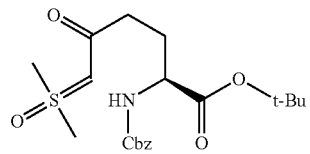

To a solution of 70.2 g (313 mmol) of trimethylsulfoxonium iodide in dehydrated N,N-dimethylformamide (585 mL), under argon atmosphere, was added 36.8 g (279 mmol) of potassium tert-butoxide, followed by stirring at room temperature for 1 hour. Then, at 5° C. or less, 87.0 g (272 mmol) of (S)-1-benzyl 2-tert-butyl 5-oxopyrrolidine-1,2-dicarboxylate was added within 20 minutes (washed with dehydrated N,N-dimethylformamide (87 mL)), followed by allowing to react at the same temperature for 1 hour. The reaction mixture was added to ice-cold water (2.6 L), saturated with sodium chloride, extracted with ethyl acetate (2.6 L×once, 1.3 L×twice, 650 mL×4 times), and the solvent of the organic layer was distilled off under reduced pressure. The resulting residue was applied to silica gel column chromatography (heptan/ethyl acetate=1/2→ethyl acetate/methanol=19/1→9/1) to afford 112.3 g of the title compound as a pale yellow oil (yield quantitative).

$^1$H NMR (400 MHz, CDCl$_3$, δ): 1.46 (s, 9H), 1.95 (m, 1H), 2.09 (m, 1H), 2.23-2.32 (m, 2H), 3.32 (s, 3H), 3.33 (s, 3H), 4.22 (m, 1H), 4.37 (s, 1H), 5.07 (d, J=12.0 Hz, 1H), 5.13 (d, J=12.0 Hz, 1H), 5.75 (br. d, J=8.0 Hz, 1H), 7.30-7.36 (m, 5H); MS m/z: 412 (M+1).

Step 3: (S)-1-Benzyl 2-tert-butyl 5-oxopiperidine-1,2-dicarboxylate

[Chemical formula 43]

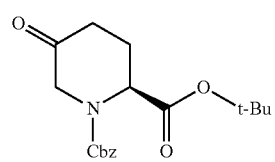

24.8 g (57.84 mmol) of (S)-tert-butyl 2-(benzyloxycarbonylamino)-5-oxo-6-dimethylsulfoxonium hexanoate was dissolved in 1,2-dichloroethane (774 mL), and, after deaeartion, 388.5 mg (0.58 mmol) of di-μ-chlorobis-[(η-cyclooct-1,5-diene)]diiridium (I) was added under argon atmosphere, followed by raising the temperature and allowing to react at +70° C. for 2 hours. The solvent of the reaction mixture was distilled off under reduced pressure, and the resulting residue was applied to silica gel column chromatography (hexane/ethyl acetate=2/1) to afford 14.55 g of the title compound as a red oil (yield 76%).

$^1$H NMR (400 MHz, CDCl$_3$, δ): 1.38 (s, 4.5H), 1.47 (s, 4.5H), 2.12-2.48 (m, 4H), 3.93 (d, J=19.0 Hz, 0.5H), 4.00 (d, J=18.8 Hz, 0.5H), 4.37 (d, J=18.8 Hz, 0.5H), 4.46 (d, J=19.0 Hz, 0.5H), 4.62 (dd, J=7.3, 6.6 Hz, 0.5H), 4.77 (dd, J=6.6, 5.9 Hz, 0.5H), 5.10-5.23 (m, 2H), 7.34-7.35 (m, 5H); MS m/z: 334 (M+1).

Step 4: (2S,5S)-1-Benzyl 2-tert-butyl 5-hydroxypiperidine-1,2-dicarboxylate (A)

[Chemical formula 44]

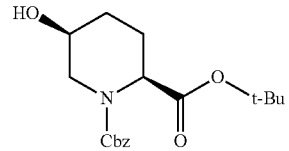

A solution of 14.55 g (43.66 mmol) of (S)-1-benzyl 2-tertbutyl 5-oxopiperidine-1,2-dicarboxylate in ethanol (437 mL) was ice-cooled, and 1.65 g (43.62 mmol) of sodium borohydride was added, followed by allowing to react under ice cooling for 20 minutes. Saturated aqueous ammonium chloride solution was added dropwise to the reaction mixture until effervescence was quenched, and the generated salt was dissolved with the addition of water. The organic solvent of the mixture was distilled off under reduced pressure, and the aqueous layer of the residue was extracted with ethyl acetate. The organic layer was washed with saturated brine, followed by drying over anhydrous magnesium sulfate, and the solvent was distilled off under reduced pressure. The resulting residue was applied to silica gel column chromatography (hexane/ethyl acetate=3/1→2/1) to afford 13.35 g of the title compound as a colorless oil (yield 91%). Enantiomeric excess: 98.8% ee (CHIRALPAK AD-H, 4.6×150 mm, UV 210 nm, hexane/ethanol=4/1, flow rate 1 mL/min., retention time 9.1 min.).

$[\alpha]^{20}_D$ −29.7°(c 1.3, CHCl$_3$), according to Non-Patent Document 1 −27.9°(c 2.0, CHCl$_3$); $^1$H NMR (400 MHz, CDCl$_3$, δ): 1.42 (s, 4.5H), 1.46 (s, 4.5H), 1.66-1.75 (m, 2H), 1.96-2.00 (m, 2H), 2.24-2.30 (m, 1H), 2.74-2.80 (m, 0.5H), 2.84-2.90 (m, 0.5H), 3.64 (brs, 1H), 4.15-4.20 (m, 0.5H), 4.23-4.27 (m, 0.5H), 4.65 (d, J=5.4 Hz, 0.5H), 4.78 (d, J=4.6 Hz, 0.5H), 5.07 (d, J=12.5 Hz, 1H), 5.21 (d, J=12.5 Hz, 1H), 7.26-7.37 (m, 5H); MS m/z: 334 (M+1).

Sequential Synthesis of (2S,5S)-1-benzyl 2-tert-butyl 5-hydroxypiperidine-1,2-dicarboxylate (A)

[Chemical formula 45]

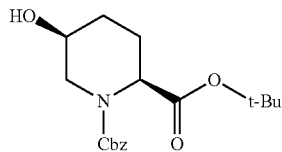

112.3 g (272 mmol) of (S)-tert-butyl 2-(benzyloxycarbonylamino)-5-oxo-6-dimethylsulfoxonium hexanoate was dissolved in 1,2-dichloroethane (3.4 L), and, after deaeartion, 1.83 g (2.72 mmol) of di-μ-chlorobis-[(η-cyclooct-1,5-diene)]diiridium (I) was added under argon atmosphere, followed by raising the temperature to +70° C. within 1.75 hours and allowing to react for 1 hour. After cooling to room temperature, the solvent of the reaction mixture was distilled off under reduced pressure, and the resulting residue was dissolved in ethanol (1.1 L). The mixture was ice-cooled, and 5.14 g (136 mmol) of sodium borohydride was added within 10 minutes, followed by allowing to react under ice cooling for 20 minutes. Saturated aqueous ammonium chloride solution (265 mL) was added dropwise to the reaction mixture until effervescence was quenched, and the generated salt was dissolved with the addition of water (250 mL). The organic solvent of the mixture was distilled off under reduced pressure, and the aqueous layer of the residue was extracted with ethyl acetate (0.9 L×3 times). The solvent was distilled off under reduced pressure, and the resulting residue was applied to silica gel column chromatography (heptan/ethyl acetate=3/1→2/1) to afford 66.82 g of the title compound as a colorless oil (yield 73%). Instrumental data were consistent with those of Step 4 of Reference Example 1.

Example 1

(2S,5S)-tert-Butyl 5-hydroxypiperidine-2-carboxylate (B)

[Chemical formula 46]

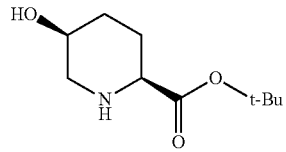

To a solution of 67.2 g (200.4 mmol) of (2S,5S)-1-Benzyl 2-tert-butyl 5-hydroxypiperidine-1,2-dicarboxylate in ethanol (900 mL) was added 10.1 g of 10% palladium-carbon (water content ca. 50%), followed by vigorous stirring overnight at room temperature under hydrogen atmosphere. The catalyst of the mixture was filtered through Celite-pad to concentrate the filtrate, whereby 39.3 g of the title compound was afforded as a colorless solid (yield 97%). Enantiomeric excess: 99% ee or more (CHIRALPAK AD-H, 4.6×150 mm, UV 210 nm, diethylamine/hexane/ethanol=0.1/80/20, flow rate 1 mL/min., retention time 6.3 min.).

$[\alpha]^{20}_D$ −28.7° (c 1.01, CHCl$_3$); $^1$H NMR (400 MHz, CDCl$_3$, δ): 1.47 (s, 9H), 1.63 (m, 1H), 1.79-1.84 (m, 3H), 2.82 (dd, J=12.2, 2.2 Hz, 1H), 3.02 (ddd, J=12.2, 3.7, 1.7 Hz, 1H), 3.21 (m, 1H), 3.80 (m, 1H); MS m/z: 202 (M+1).

Example 2

(2S,5S)-tert-Butyl 5-hydroxy-1-(2,2,2-trifluoroacetyl)piperidine-2-carboxylate (C)

[Chemical formula 47]

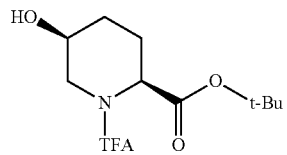

A solution of 39.14 g (194 mmol) of (2S,5S)-tert-butyl 5-hydroxypiperidine-2-carboxylate in dehydrated tetrahydrofuran (450 mL) was cooled to −3 to −5° C. under argon atmosphere, and 78.7 g (776 mmol) of triethylamine was added, followed by dropwise addition of 81.5 g (388 mmol) of trifluoroacetic acid anhydride over 30 minutes. The reaction mixture was allowed to react at −3 to −5° C. for 1 hour, and water (90 mL) was added, followed by raising the temperature to room temperature and stirring for 1 hour. Water (740 mL) was added to the reaction mixture, followed by extraction with ethyl acetate (450 mL×3 times), and the combined organic layer was washed sequentially with 5% aqueous citric acid solution (450 mL), 6.5% aqueous sodium hydrogencarbonate solution (450 mL) and water (450 mL). The solvent was distilled off under reduced pressure, and the resulting residue was applied to silica gel column chromatography (hexane/ethyl acetate=2/1) to afford 50.06 g of the title compound as a pale yellow solid (yield 87%). Enantiomeric excess: 99% ee or more (CHIRALPAK AD-H, 4.6×

150 mm, UV 210 nm, hexane/ethanol=4/1, flow rate 1 mL/min., retention time 4.2 min.).

$[\alpha]^{20}{}_D$–54.1°(c 0.73, CHCl$_3$); $^1$H NMR (400 MHz, CDCl$_3$, δ): observed as a mixture of 2 rotamers (7:3). 1.26-1.43 (m, 1H), 1.46 (s, 2.7H), 1.47 (s, 6.3H), 1.68-1.77 (m, 1H), 1.81 (d, J=4.8 Hz, 0.3H), 1.89 (d, J=5.2 Hz, 0.7H), 2.05-2.08 (m, 1H), 2.36-2.42 (m, 1H), 2.77 (dd, J=12.2, 12.0 Hz, 0.3H), 3.12 (dd, J=13.2, 10.7 Hz, 0.7H), 3.68-3.77 (m, 1H), 4.00 (m, 1H), 4.52-4.60 (m, 0.6H), 5.07 (d, J=5.9 Hz, 0.7H); MS m/z: 298 (M+1).

Example 3

(2S,5R)-tert-Butyl 5-(benzyloxyamino)-1-(2,2,2-trifluoroacetyl)piperidine-2-carboxylate (D)

[Chemical formula 48]

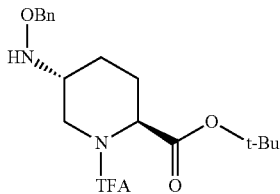

After a solution of 10.22 g (34.38 mmol) of (2S,5S)-tert-butyl 5-hydroxy-1-(2,2,2-trifluoroacetyl)piperidine-2-carboxylate in dehydrated acetonitrile (113 mL) was cooled from −30 to −40° C. under argon atmosphere, 4.4 mL (37.78 mmol) of 2,6-lutidine was added, and then 5.92 mL (36.09 mmol) of trifluoromethanesulfonic acid anhydride was added dropwise over 10 minutes, followed by further allowing to react at −30° C. for 15 minutes. To this reaction mixture was added 8.46 g (68.73 mmol) of benzyloxyamine (washed with acetonitrile (5 mL)), followed by raising the temperature to 0° C. within 30 minutes, and further 4.4 mL (37.78 mmol) of 2,6-lutidine was added, followed by allowing to react at 0 to 5° C. for 3.5 days. This reaction mixture was concentrated under reduced pressure, and the resulting residue was diluted with ethyl acetate (200 mL) and washed sequentially with water (200 mL), 10% aqueous citric acid solution (200 mL×3 times), 6.5% aqueous sodium hydrogencarbonate solution (100 mL) and saturated brine (100 mL). Each aqueous layer was back-extracted with ethyl acetate (100 mL), the organic layers were combined and dried over anhydrous magnesium sulfate, and the solvent was distilled off under reduced pressure. The resulting residue was applied to silica gel column chromatography (hexane/ethyl acetate=4/1) to afford 11.69 g of the title compound as a colorless oil (yield 85%). Enantiomeric excess: 99.0% ee (CHIRALPAK AD-H, 4.6×150 mm, UV 210 nm, hexane/ethanol=9/1, flow rate 1 mL/min., retention time 4.5 min.).

$[\alpha]^{20}{}_D$–45.6°(c 0.73, CHCl$_3$); $^1$H NMR (400 MHz, CDCl$_3$, δ): observed as a mixture of 2 rotamers (7 to 3). 1.46 (s, 2.7H), 1.48 (s, 6.3H), 1.62-1.65 (m, 2H), 1.93-2.05 (m, 2H), 3.13 (m, 0.3H), 3.24-3.29 (m, 1H), 3.46 (m, 0.7H), 4.12 (m, 0.3H), 4.58-4.77 (m, 2.7H), 5.06 (m, 0.7H), 5.38 (m, 1H), 7.30-7.36 (m, 5H); MS m/z: 403 (M+1).

Example 4

(2S,5R)-tert-Butyl 5-(benzyloxyamino)piperidine-2-carboxylate (E)

[Chemical formula 49]

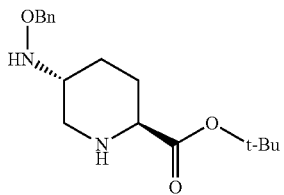

Water (9.2 mL) was added to a solution of 6.91 g (17.17 mmol) of (2S,5R)-tert-butyl 5-(benzyloxyamino)-1-(2,2,2-trifluoroacetyl)piperidine-2-carboxylate in 1,4-dioxane (34 mL), and, under ice cooling, 2.5M NaOH (13.7 mL) was added dropwise, followed by allowing to react at the same temperature for 0.5 hours. Acetic acid (ca. 1 mL) was added to the reaction mixture, followed by concentration under reduced pressure, and subsequently the resulting concentrated residue was extracted with ethyl acetate (58 mL, 29 mL). After the organic layers were washed respectively with 50% aqueous potassium carbonate solution, they were combined, followed by drying with anhydrous sodium sulfate, and the solvent was distilled off under reduced pressure. The resulting residue was applied to silica gel column chromatography (hexane/ethyl acetate=4/1→0/1→ethyl acetate/methanol=19/1) to afford 4.74 g of the title compound as a colorless oil (yield 90%). Enantiomeric excess: 98.9% ee (CHIRALPAK AD-H, 4.6×150 mm, UV 210 nm, diethylamine/hexane/ethanol=0.1/80/20, flow rate 1 mL/min., retention time 5.5 min.).

$[\alpha]^{20}{}_D$–2.8°(c 0.73, CHCl$_3$); $^1$H NMR (400 MHz, CDCl$_3$, δ): 1.28 (m, 1H, 1.42-1.46 (m, 10H), 1.92 (m, 1H), 2.04 (ddd, J=12.9, 7.3, 4.0 Hz, 1H), 2.43 (dd, J=12.0, 9.8 Hz, 1H), 2.98 (m, 1H), 3.16 (dd, J=11.0, 3.2 Hz, 1H), 3.57 (ddd, J=12.0, 4.2, 2.0 Hz, 1H), 4.68 (s, 2H), 7.29-7.35 (m, 5H); MS m/z: 307 (M+1).

Example 5

Sequential Synthesis of (2S,5R)-tert-butyl 5-(benzyloxyamino)piperidine-2-carboxylate (E)

[Chemical formula 50]

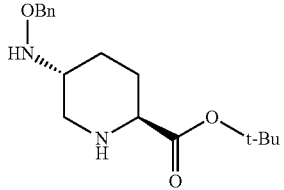

A solution of 47.9 g (161 mmol) of (2S,5S)-tert-butyl 5-hydroxy-1-(2,2,2-trifluoroacetyl)piperidine-2-carboxylate in dehydrated acetonitrile (318 mL) was cooled from −30 to −40° C. under argon atmosphere, and 20.5 mL (177 mmol) of 2,6-lutidine was added, and then 28.4 mL (169 mmol) of trifluoromethanesulfonic acid anhydride was added dropwise over 40 minutes, followed by further allowing to react at −30° C. for 15 minutes. To this reaction mixture was added 39.7 g (322 mmol) of benzyloxyamine (washed with acetonitrile (11 mL)) within 8 minutes, followed by raising the temperature to 0° C. within 30 minutes, and further 20.5 mL (177 mmol) of 2,6-lutidine was added, followed by allowing to react at 0 to 5° C. for 2 days. This reaction mixture was concentrated under reduced pressure, and the resulting residue was diluted with ethyl acetate (960 mL) and washed sequentially with water (960 mL), 10% aqueous citric acid solution (960 mL×3 times), 6.5% aqueous sodium hydrogencarbonate solution (480 mL) and saturated brine (480 mL). Each aqueous layer was back-extracted with ethyl acetate (960 mL), the organic layers were combined, and the solvent was distilled off under reduced pressure. The resulting residue was dissolved in 1,4-dioxane (320 mL) solution and water (86 mL), and, under ice cooling, 2.5M NaOH (128 mL) was added dropwise, followed by allowing to react at the same temperature for 0.5 hours. Acetic acid (ca. 9.3 mL) was added to the reaction mixture, followed by concentration under reduced pressure, and subsequently the resulting concentrated residue was extracted with ethyl acetate (580 mL, 290 mL). After the organic layers were washed respectively with 50% aqueous potassium carbonate solution (580 mL), they were combined, and the solvent was distilled off under reduced pressure. The resulting residue was applied to silica gel column chromatography (hexane/ethyl acetate=4/1→0/1→ethyl acetate/methanol=100/1→19/1) to afford 36.58 g of the title compound as a colorless oil (yield 74%). Instrumental data were consistent with those of Example 4.

Example 6

(2S,5R)-tert-Butyl 6-(benzyloxy)-7-oxo-1,6-diazabicyclo[3.2.1]octane-2-carboxylate (F1)

[Chemical formula 51]

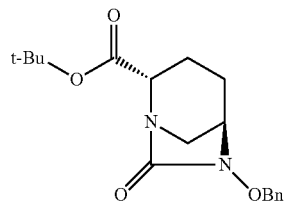

To a solution of 4.14 g (13.51 mmol) of (2S,5R)-tert-butyl 5-(benzyloxyamino) piperidine-2-carboxylate in dehydrated acetonitrile (615 mL), under argon atmosphere, at 0° C., was added triethylamine 4.9 mL (35.16 mmol), and subsequently 1.18 mL (9.78 mmol) of diphosgene was added dropwise within 5 minutes, followed by stirring at the same temperature for 10 minutes. 182 mg (1.623 mmol) of 4-dimethylaminopyridine was added to this solution, and the temperature was raised to room temperature, followed by allowing to react for 3 hours. After the reaction mixture was concentrated under reduced pressure to the volume of one tenth thereof, the resulting concentrated solution was diluted with ethyl acetate, washed sequentially with water, 5% aqueous citric acid solution, 6.5% aqueous sodium hydrogencarbonate solution and saturated brine and dried over anhydrous magnesium sulfate, and the solvent was distilled off under reduced pressure. The resulting residue was applied to silica gel column chromatography (hexane/ethyl acetate=2/1) to afford 3.09 g of the title compound (yield 69%). The resulting solid was recrystallized from ethyl acetate-hexane, and the generated precipitate was filtered off. The wet crystal was washed with hexane, and subsequently dried under reduced pressure at room temperature to afford the title compound as a colorless crystalline powder. Enantiomeric excess: 99.4% ee (CHIRALPAK AD-H, 4.6×150 mm, hexane/ethanol=2/1, UV 210 nm, flow rate 1 mL/min., retention time 8.0 min.).

Mp 83° C.; $[\alpha]^{20}_D$+5.9°(c 0.61, CHCl$_3$); $^1$H NMR (400 MHz, CDCl$_3$, δ): 1.48 (s, 9H), 1.62 (m, 1H), 2.00-2.10 (m, 3H), 2.98 (d, J=11.7 Hz, 1H), 3.03 (m, 1H), 3.30 (m, 1H), 4.01 (m, 1H), 4.90 (d, J=11.5 Hz, 1H), 5.06 (d, J=11.5 Hz, 1H), 7.35-7.42 (m, 5H); MS m/z: 333 (M+1).

In powder X-ray diffraction diagram, the crystal of the title compound demonstrated characteristic peak patterns as shown in the following Table 8. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 8

| Powder X-ray Diffraction of Compound (F1) | | |
|---|---|---|
| Peak Position | | |
| 2θ (CuKα) | Spacing (d) Å | Relative Intensity I/I0 |
| 7.64 | 11.56 | 13 |
| 8.06 | 10.96 | 67 |
| 13.50 | 6.55 | 46 |
| 14.74 | 6.00 | 15 |
| 15.30 | 5.79 | 11 |
| 15.92 | 5.56 | 44 |
| 16.18 | 5.47 | 58 |
| 16.86 | 5.25 | 64 |
| 18.10 | 4.90 | 46 |
| 20.38 | 4.35 | 18 |
| 20.96 | 4.23 | 100 |
| 23.04 | 3.86 | 10 |

Example 7

(2S,5R)-tert-Butyl 6-(benzyloxy)-7-oxo-1,6-diazabicyclo[3.2.1]octane-2-carboxylate (F1)

Reaction by Phosgene Gas

To a solution of 3.0 g (9.791 mmol) of (2S,5R)-tert-Butyl 5-(benzyloxyamino) piperidine-2-carboxylate in dehydrated acetonitrile (150 mL), under argon atmosphere, at room temperature, were added 3.82 mL (27.4 mmol) of triethylamine and 120 mg (0.979 mmol) of 4-dimethylaminopyridine, and phosgene gas (generated by adding 1.548 g (7.83 mmol) of diphosgene dropwise on the activated carbon (1 g) at 60° C. within 1.5 hours) was introduced by means of an argon stream, followed by stirring overnight. Excess phosgene was decomposed with concentrated aqueous ammonia (0.6 mL), and the solvent of the reaction mixture was concentrated under reduced pressure. The residue was diluted with ethyl acetate (50 mL), washed sequentially with water (50 mL), 5% aqueous citric acid solution (50 mL), 6.5% aqueous sodium hydrogencarbonate solution (25 mL)

and saturated brine (25 mL) and dried over anhydrous magnesium sulfate, and the solvent was distilled off under reduced pressure. The resulting residue was applied to silica gel column chromatography (hexane/ethyl acetate=2/1) to afford 2.25 g of the title compound (yield 69%). The resulting solid was recrystallized with ethyl acetate-hexane, and the generated precipitate was filtered off. The wet crystal was washed with hexane, and subsequently dried under reduced pressure at room temperature to afford the title compound as a colorless crystalline powder. Instrumental data were consistent with those of the title compound of Example 6.

Example 8

Cyclohexylamine Salt of (2S,5R)-6-(benzyloxy)-7-oxo-1,6-diazabicyclo[3.2.1]octane-2-carboxylic acid (F1-1a)

[Chemical formula 52]

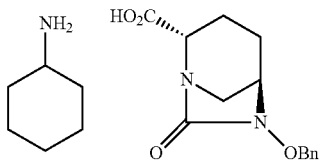

To a solution of 270 mg (0.842 mmol) of (2S,5R)-tert-butyl 6-(benzyloxy)-7-oxo-1,6-diazabicyclo[3.2.1]octane-2-carboxylate in dichloromethane (2 mL), under argon atmosphere, at 0° C., was added trifluoroacetic acid (2 mL), and the temperature was raised to room temperature, followed by allowing to react for 4 hours. The reaction mixture was concentrated, and the resulting residue was diluted with ethyl acetate, washed sequentially with water and saturated brine and dried over anhydrous magnesium sulfate, and the solvent was distilled off under reduced pressure. The resulting residue was dissolved in ethyl acetate (2.5 mL), and a solution of 149 mg of cyclohexylamine in diethylether was added at room temperature, followed by stirring at 0° C. for 1 hour. The generated precipitate was filtered off, and the filter cake was washed with diethylether, and subsequently dried under reduced pressure at room temperature to afford 270 mg of the title compound as a colorless crystalline powder (yield 86%).

Mp 175° C.; $[\alpha]^{20}_D$ −36.8°(c 0.50, H$_2$O); $^1$H NMR (400 MHz, DMSO-d6, δ): 1.00-1.30 (m, 5H), 1.53-1.95 (m, 8H), 2.04-2.09 (m, 1H), 2.76 (d, J=11.6 Hz, 1H), 2.80-2.93 (m, 1H), 3.19 (d, J=11.2 Hz, 1H), 3.33 (brs, 2H), 3.40 (d, J=7.2 Hz, 1H), 3.51 (brs, 1H), 4.87 (d, J=11.6 Hz, 1H), 4.93 (d, J=11.6 Hz, 1H), 7.30-7.45 (m, 5H), 8.04 (brs, 1H); MS m/z: 100, 277 (M+1).

In powder X-ray diffraction diagram, the crystal of the title compound demonstrated characteristic peak patterns as shown in the following Table 9. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 9

Powder X-ray Diffraction of Compound (F1-1a)

| 2θ (Cukα) | Spacing (d) Å | Relative Intensity I/I0 |
|---|---|---|
| 8.88 | 9.95 | 46 |
| 10.46 | 8.45 | 9 |
| 14.14 | 6.26 | 14 |
| 15.08 | 5.87 | 17 |
| 16.04 | 5.52 | 100 |
| 16.98 | 5.22 | 71 |
| 17.38 | 5.10 | 17 |
| 17.88 | 4.96 | 26 |
| 18.74 | 4.73 | 57 |
| 19.52 | 4.54 | 22 |
| 21.36 | 4.16 | 13 |
| 22.60 | 3.93 | 68 |
| 25.08 | 3.55 | 12 |

Example 9

(2S,5R)-6-(Benzyloxy)-7-oxo-1,6-diazabicyclo[3.2.1]octane-2-carboxylic acid (F1-2)

[Chemical formula 53]

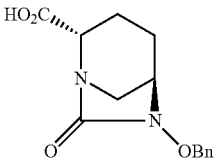

230 mg of cyclohexylamine salt of (2S,5R)-6-(benzyloxy)-7-oxo-1,6-diazabicyclo[3.2.1]octane-2-carboxylic acid was dissolved in saturated aqueous sodium dihydrogen phosphate solution, followed by extraction 4 times with ethyl acetate, and the combined organic layer was washed with saturated brine, and subsequently dried over anhydrous magnesium sulfate. The solvent was distilled off under reduced pressure, and dried under vacuum, to afford 161 mg of the title compound as a colorless foamy solid (yield 87%). Enantiomeric excess: 99.9% ee or more (CHIRALPAK AD-H, 4.6×150 mm, trifluoroacetic acid/hexane/ethanol=0.1/80/20, UV 210 nm, flow rate 1 mL/min., retention time 10.5 min.).

$[\alpha]^{20}_D$+11.5°(c 0.56, CHCl$_3$); $^1$H NMR (400 MHz, CDCl$_3$, δ): 1.67 (m, 1H), 2.04-2.26 (m, 3H), 2.85 (d, J=12.0 Hz, 1H), 3.13 (m, 1H), 3.35 (m, 1H), 4.12 (m, 1H), 4.91 (d, J=11.3 Hz, 1H), 5.06 (d, J=11.3 Hz, 1H), 7.37-7.44 (m, 5H); MS m/z: 277 (M+1).

Example 10

(2S,5R)-6-(Benzyloxy)-7-oxo-1,6-diazabicyclo[3.2.1]octane-2-carboxylic acid (F1-2), treatment with diluted hydrochloric acid followed by crystallization 3.75 g (10.0 mmol) of (2S,5R)-6-(benzyloxy)-7-oxo-1,6-diazabicyclo[3.2.1]octane-2-carboxylic acid cyclohexylamine salt was dissolved in 50 ml of water, and 100 ml of ethyl acetate and 20 ml of 1 N hydrochloric acid were added. The mixture was stirred, followed by extraction with ethyl acetate (100 ml, each time) 3 times. The organic layer was dried with anhydrous magnesium sulfate, and the solvent was concentrated to 10 ml under reduced pressure. 120 ml of hexane was gradually added while stirring under cooling with ice and the resulting precipitate was filtered off. The moist crystal was washed with hexane, and dried at room temperature under reduced pressure to afford 2.44 g (8.83 mmol) of the title compound as a colorless crystalline powder.

Mp 116° C.; the other instrumental data were consistent with those of the title compound of Example 9.

In powder X-ray diffraction diagram, the crystal of the title compound demonstrated characteristic peak patterns as shown in the following Table 10. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 10

Powder X-ray diffraction of compound (F1-2)

| Peak position | | |
|---|---|---|
| 2θ (Cukα) | Lattice spacing (d) Å | Relative intensity I/I0 |
| 10.80 | 8.19 | 10 |
| 12.38 | 7.14 | 14 |
| 13.32 | 6.64 | 11 |
| 14.06 | 6.29 | 81 |
| 15.82 | 5.60 | 33 |
| 17.02 | 5.21 | 92 |
| 18.04 | 4.91 | 12 |
| 19.28 | 4.60 | 37 |
| 21.06 | 4.21 | 100 |
| 24.08 | 3.69 | 42 |
| 25.80 | 3.45 | 16 |
| 28.52 | 3.13 | 33 |

Example 11

(2S,5R)-6-(benzyloxy)-7-oxo-1,6-diazabicyclo[3.2.1]octane-2-carboxylic acid (F1-2), Synthesis from (F1-3a)

[Chemical formula 54]

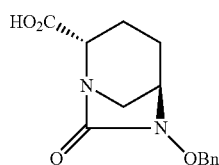

To a solution of 100 mg (0.345 mmol) of (2S,5R)-methyl 6-(benzyloxy)-7-oxo-1,6-diazabicyclo[3.2.1]octane-2-carboxylate in tetrahydrofuran (3 mL) was added water (3 mL), followed by cooling to 0° C., and 15.2 mg (0.362 mmol) of lithium hydroxide monohydrate was added, followed by stirring at the same temperature for 15 minutes. The reaction mixture was washed with ethyl acetate, and the aqueous layer was made acidic with saturated aqueous sodium dihydrogen phosphate solution, followed by extraction with ethyl acetate. The organic layer was washed with saturated brine, dried over anhydrous magnesium sulfate, and subsequently the solvent was concentrated under reduced pressure to afford 93.1 mg of the title compound as a colorless foamy solid (yield 98%). Instrumental data were consistent with those of Example 9.

Example 12

(2S,5R)-6-(benzyloxy)-7-oxo-1,6-diazabicyclo[3.2.1]octane-2-carboxylic acid (F1-2), Synthesis from (F1-3b)

[Chemical formula 55]

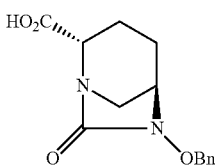

To a solution of 100 mg (0.316 mmol) of (2S,5R)-allyl 6-(benzyloxy)-7-oxo-1,6-diazabicyclo[3.2.1]octane-2-carboxylate in dichloromethane (2 mL) were added a solution of 0.5M sodium 2-ethylhexanoate in ethyl acetate (1 mL) and 12 mg of tetrakis(triphenylphosphine)palladium(0), followed by stirring at room temperature for 1 hour. The reaction mixture was diluted with ethyl acetate, followed by liquid separation with saturated aqueous sodium dihydrogen phosphate solution, the aqueous layer was extracted twice with ethyl acetate, and the combined organic layer was dried over anhydrous sodium sulfate. The residue resulting from concentration of the solvent under reduced pressure was dissolved in ethyl acetate, followed by addition of cyclohexylamine (33 mg), and the deposited solid was filtered off, and washed with ether. The resulting solid was dissolved in saturated aqueous sodium dihydrogen phosphate solution, followed by extraction with ethyl acetate, and the organic layer was washed with saturated brine and dried over anhydrous magnesium sulfate. Subsequently, the solvent was concentrated under reduced pressure to afford 68 mg of the title compound as a colorless foamy solid (yield 75%). Instrumental data were consistent with those of the compound of Example 9.

Example 13

(2S,5R)-Methyl 6-(benzyloxy)-7-oxo-1,6-diazabicyclo[3.2.1]octane-2-carboxylate (F1-3a)

[Chemical formula 56]

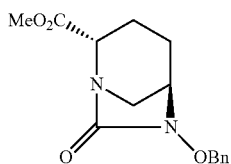

66 mg (0.239 mmol) of (2S,5R)-6-(benzyloxy)-7-oxo-1,6-diazabicyclo[3.2.1]octane-2-carboxylic acid was dissolved in toluene (0.6 mL) and methanol (0.6 mL), and, under ice cooling, 0.54 mL (0.324 mmol) of 0.6 M trimethylsilyldiazomethane-hexane solution was added, followed by stirring for 20 minutes. The reaction solution was concentrated under reduced pressure, and the resulting residue was subjected to silica gel column chromatography (hexane/ethyl acetate=2/1) to afford 21.5 mg of the title compound as a colorless solid (yield 31%). The resulting solid was recrystallized with ethyl acetate-hexane, the generated precipitate was filtered off, the wet crystal was washed with hexane, and subsequently dried under reduced pressure at room temperature to afford the title compound as a colorless crystalline powder. Enantiomeric excess: 99.9% ee or more (CHIRALPAK AD-H, 4.6×150 mm, hexane/ethanol=2/1, UV 210 nm, flow rate 1 mL/min., retention time 12.8 min.).

Mp 86° C.; $[\alpha]^{20}_D$+5.3°(c 1.10, CHCl$_3$); $^1$H NMR (400 MHz, CDCl$_3$, δ): 1.65-1.70 (m, 1H), 2.03-2.12 (m, 3H), 2.90 (d, J=12.0 Hz, 1H), 3.07 (m, 1H), 3.79 (s, 3H), 4.12 (dd, J=4.6, 4.4 Hz, 1H), 4.91 (d, J=11.2 Hz, 1H), 5.06 (d, J=11.2 Hz, 1H), 7.35-7.44 (m, 5H); MS m/z: 291 (M+1).

In powder X-ray diffraction diagram, the crystal of the title compound demonstrated characteristic peak patterns as shown in the following Table 11. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 11

Powder X-ray Diffraction of Compound (F1-3a)

| 2θ (Cuka) | Spacing (d) Å | Relative Intensity I/I0 |
|---|---|---|
| 8.50 | 10.39 | 92 |
| 15.10 | 5.86 | 9 |
| 15.56 | 5.69 | 66 |
| 16.60 | 5.34 | 11 |
| 18.42 | 4.81 | 28 |
| 19.98 | 4.44 | 100 |
| 22.30 | 3.98 | 9 |
| 23.50 | 3.78 | 66 |
| 28.64 | 3.11 | 13 |
| 29.44 | 3.03 | 19 |
| 30.52 | 2.93 | 13 |
| 32.28 | 2.77 | 11 |

Example 14

(2S,5R)-Allyl 6-(benzyloxy)-7-oxo-1,6-diazabicyclo[3.2.1]octane-2-carboxylate (F1-3b)

[Chemical formula 57]

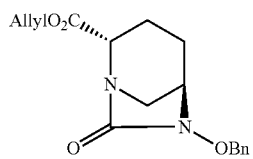

46 mg of (2S,5R)-6-(benzyloxy)-7-oxo-1,6-diazabicyclo[3.2.1]octane-2-carboxylic acid was dissolved in N,N-dimethylformamide (0.5 mL), and 21 mg of sodium hydrogen carbonate and 30 μL of allyl bromide were added, followed by stirring for 6.5 hours. Ethyl acetate was added to the reaction solution, followed by sequential washing with water and saturated brine and drying over anhydrous sodium sulfate, and the solvent was concentrated under reduced pressure. The resulting residue was subjected to silica gel column chromatography (hexane/ethyl acetate=3/1) to afford 7.5 mg of the title compound as a colorless solid (yield 14%). The resulting solid was recrystallized from ethyl acetate-hexane, the generated precipitate was filtered off, the wet crystal was washed with hexane, and subsequently dried under reduced pressure at room temperature to afford the title compound as a colorless crystalline powder. Enantiomeric excess: 99.9% ee or more (CHIRALPAK AD-H, 4.6×150 mm, hexane/ethanol=2/1, UV 210 nm, flow rate 1 mL/min., retention time 8.0 minutes).

Mp 60-62° C.; $[\alpha]^{20}_D$+4.0°(c 1.05, CHCl$_3$); $^1$H NMR (400 MHz, CDCl$_3$, δ): 1.69 (m, 1H), 2.02-2.15 (m, 3H), 2.93 (d, J=12.0 Hz, 1H), 3.07 (m, 1H), 3.31 (m, 1H), 4.14 (dd, J=6.5, 2.6 Hz, 1H), 4.67 (ddd, J=5.9, 1.5, 1.2 Hz, 1H), 4.91 (d, J=11.5 Hz, 1H), 5.06 (d, J=11.5 Hz, 1H), 5.26 (m, 1H), 5.34 (m, 1H), 5.92 (m, 1H), 7.36-7.42 (m, 5H); MS m/z: 317 (M+1).

In powder X-ray diffraction diagram, the crystal of the title compound demonstrated characteristic peak patterns as shown in the following Table 10. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 12

Powder X-ray Diffraction of Compound (F1-3b)

| 2θ (Cuka) | Spacing (d) Å | Relative Intensity I/I0 |
|---|---|---|
| 6.00 | 14.72 | 100 |
| 18.06 | 4.91 | 26 |
| 19.88 | 4.46 | 10 |
| 20.94 | 4.24 | 10 |
| 24.22 | 3.67 | 12 |

Example 15

(2S,5R)-Benzyl 6-(benzyloxy)-7-oxo-1,6-diazabicyclo[3.2.1]octane-2-carboxylate (F1-3c)

[Chemical formula 58]

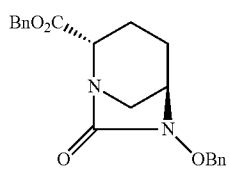

94 mg (0.346 mmol) of (2S,5R)-6-(benzyloxy)-7-oxo-1,6-diazabicyclo[3.2.1]octane-2-carboxylic acid was dissolved in dichloromethane (3.4 mL), and 70 μL (0.676 mmol) of benzylalcohol and 98 mg (0.511 mmol) of 1-ethyl-3-(3-dimethylaminopropyl) carbodiimide hydrochloride were added, followed by stirring at room temperature for 24 hours. The reaction mixture was concentrated under reduced pressure, and subsequently the residue was diluted with ethyl acetate and washed with water and then with saturated brine. The organic layer was dried over anhydrous magnesium sulfate, and the solvent was concentrated under reduced pressure. The resulting residue was applied to silica gel column chromatography (hexane/ethyl acetate=3/1) to afford 41.2 mg of the title compound (yield 33%). Enantiomeric excess: 99.8% ee (CHIRALPAK AD-H, 4.6×150 mm, hexane/ethanol=2/1, UV 210 nm, flow rate 1 mL/min., retention time 33.2 min.).

$[\alpha]^{20}_D$+3.3°(c 0.82, CHCl$_3$); $^1$H NMR (400 MHz, CDCl$_3$, δ): 1.58-1.65 (m, 1H), 2.01-2.12 (m, 3H), 2.86 (d, J=12.0 Hz, 1H), 3.03 (m, 1H), 3.28 (m, 1H), 4.15 (m, 1H), 4.89 (d, J=11.5 Hz, 1H), 5.05 (d, J=11.5 Hz, 1H), 5.22 (s, 2H), 7.26-7.43 (m, 10H); MS m/z: 367 (M+1).

Example 16

(2S,5R)-2,5-Dioxopyrrolidin-1-yl 6-(benzyloxy)-7-oxo-1,6-diazabicyclo[3.2.1]octane-2-carboxylate (F1-3d)

[Chemical formula 59]

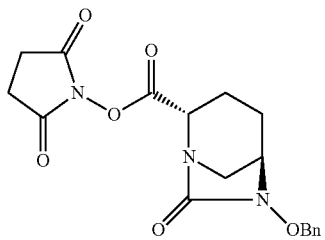

201 mg of (2S,5R)-6-(benzyloxy)-7-oxo-1,6-diazabicyclo[3.2.1]octane-2-carboxylic acid was dissolved in dehydrated dichloromethane (3.6 mL), and 162 mg of N-methylmorpholin was added, followed by cooling to 0° C. 198.8 mg of isobutyl chloroformate was added to the mixture, followed by stirring for 10 minutes, and subsequently 167 mg of N-hydroxysuccinimide was added, followed by further stirring for 0.5 hours. The reaction mixture was washed with water and dried over anhydrous magnesium sulfate, and the solvent was concentrated under reduced pressure. The resulting residue was applied to silica gel column chromatography (hexane/ethyl acetate=1/2) to afford 161 mg of the title compound as a colorless solid (yield 59%).

$[\alpha]^{20}_D$+4.76°(c 0.88, CHCl$_3$); $^1$H NMR (400 MHz, CDCl$_3$, δ): 1.74 (m, 1H), 2.08 (m, 1H), 2.16-2.29 (m, 2H), 2.85 (m, 4H), 3.11-3.18 (m, 2H), 3.34 (s, 1H), 4.48 (d, J=6.4 Hz, 1H), 4.92 (d, J=11.2 Hz, 1H), 5.06 (d, J=11.2 Hz, 1H), 7.35-7.45 (m, 5H); MS m/z: 274 (M+1).

Example 17

(2S,5R)-tert-Butyl 6-(allyloxy)-7-oxo-1,6-diazabicyclo[3.2.1]octane-2-carboxylate (F2)

[Chemical formula 60]

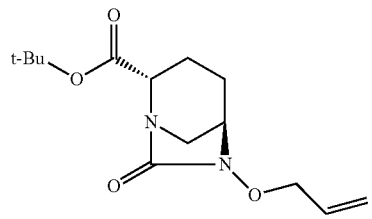

140 mg (0.421 mmol) of (2S,5R)-tert-butyl 6-(benzyloxy)-7-oxo-1,6-diazabicyclo[3.2.1]octane-2-carboxylate was dissolved in ethanol (3.1 mL), and 14 mg of 10% palladium-carbon (50% water content) was added, followed by stirring at room temperature for 1 hour under hydrogen atmosphere. The catalyst of the reaction mixture was filtered through celite, and the residue resulting from concentration of the solvent under reduced pressure was dissolved in acetonitrile (4.1 mL), and 62 mg (0.449 mmol) of anhydrous potassium carbonate and 70 μL (0.809 mmol) of allyl bromide were added, followed by stirring at room temperature for 3 hours. After the reaction mixture was concentrated under reduced pressure, the residue was diluted with ethyl acetate and washed sequentially with water, saturated aqueous ammonium chloride solution and saturated brine, subsequently the organic layer was dried over anhydrous magnesium sulfate, and the solvent was concentrated under reduced pressure. The resulting residue was applied to silica gel column chromatography (n-hexane/ethyl acetate=5/2) to afford 60.8 mg of the title compound (yield 54%). Enantiomeric excess: 99.9% ee or more (CHIRALPAK AD-H, 4.6×150 mm, hexane/ethanol=2/1, UV 210 nm, flow rate 1 mL/min., retention time 4.8 min.).

$[\alpha]^{20}_D$−39.3°(c 1.11, CHCl$_3$); $^1$H NMR (400 MHz, CDCl$_3$, δ): 1.50 (s, 9H), 1.70-1.80 (m, 1H), 2.04-2.12 (m, 3H), 3.08 (d, J=12.0 Hz, 1H), 3.14 (m, 1H), 3.74 (m, 1H), 4.01 (m, 1H), 4.45 (m, 2H), 5.29-5.39 (m, 2H), 5.98-6.08 (m, 1H); MS m/z: 283 (M+1).

Example 18

Cyclohexylamine salt of (2S,5R)-6-(allyloxy)-7-oxo-1,6-diazabicyclo[3.2.1]octane-2-carboxylic acid (F2-1a)

[Chemical formula 61]

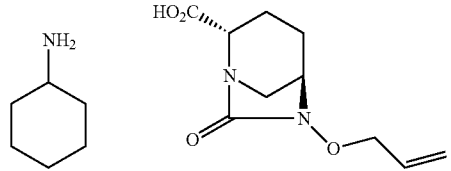

From (2S,5R)-tert-butyl 6-(allyloxy)-7-oxo-1,6-diazabicyclo[3.2.1]octane-2-carboxylate, according to the method of Example 8, the title compound was afforded as a colorless solid.

[α]$^{20}_D$ −44.4° (c 0.25, H$_2$O); $^1$H NMR (400 MHz, D$_2$O, δ): 0.95-1.24 (m, 5H), 1.48-1.81 (m, 8H), 2.02 (dd, J=14.6, 7.1 Hz, 1H), 2.92 (d, J=11.7 Hz, 1H), 3.00 (m, 1H), 3.62 (d, J=7.6 Hz, 1H), 3.88 (s, 1H), 4.33-4.36 (m, 2H), 5.23-5.33 (m, 2H), 5.85-5.95 (m, 1H); MS m/z: 100, 227 (M+1).

Example 19

(2S,5R)-6-(Allyloxy)-7-oxo-1,6-diazabicyclo[3.2.1]octane-2-carboxylic acid (F2-2)

[Chemical formula 62]

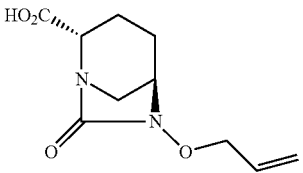

From the cyclohexylamine salt of (2S,5R)-6-(allyloxy)-7-oxo-1,6-diazabicyclo[3.2.1]octane-2-carboxylic acid, according to the method of Example 9, the title compound was afforded. Enantiomeric excess: 99.9% ee or more (CHIRALPAK AD-H, 4.6×150 mm, trifluoroacetic acid/hexane/ethanol=0.1/80/20, UV 210 nm, flow rate 1 mL/min., retention time 5.5 min.).

[α]$^{20}_D$ −32.3° (c 1.59, CHCl$_3$); $^1$H NMR (400 MHz, CDCl$_3$, δ): 1.60-1.81 (m, 1H), 2.01-2.13 (m, 2H), 2.25-2.31 (m, 1H), 3.07 (d, J=11.7 Hz, 1H), 3.33 (br.d J=11.2 Hz, 1H), 3.86 (s, 1H), 4.19 (d, J=7.3 Hz, 1H), 4.42-4.52 (m, 2H), 5.33-5.42 (m, 2H), 5.96-6.06 (m, 1H); MS m/z: 227 (M+1).

Example 20

(2S,5R)-Benzyl 6-(allyloxy)-7-oxo-1,6-diazabicyclo[3.2.1]octane-2-carboxylate (F2-3c)

[Chemical formula 63]

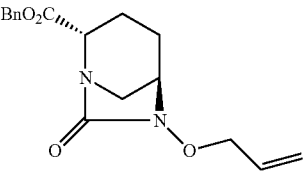

From (2S,5R)-6-(allyloxy)-7-oxo-1,6-diazabicyclo[3.2.1]octane-2-carboxylic acid, according to the method of Example 14, the title compound was afforded. Enantiomeric excess: 98.5% ee. (CHIRALPAK AD-H, 4.6×150 mm, hexane/ethanol=2/1, UV 210 nm, flow rate 1 mL/min., retention time 15.5 min.).

[α]$^{20}_D$ −42.5° (c 0.252, CHCl$_3$); $^1$H NMR (400 MHz, CDCl$_3$, δ): 1.67-1.77 (m, 1H), 2.08-2.15 (m, 3H), 2.97 (d, J=12.0 Hz, 1H), 3.14 (m, 1H), 3.73 (m, 1H), 4.16 (m, 1H), 4.39-4.51 (m, 2H), 5.23 (m, 2H), 5.29-5.38 (m, 2H), 5.96-6.05 (m, 1H), 7.33-7.38 (m, 5H); MS m/z: 317 (M+1).

Example 21

(2S,5R)-6-(benzyloxy)-7-oxo-1,6-diazabicyclo[3.2.1]octane-2-carboxamide (F1-4), Synthesis from (F1-3d)

[Chemical formula 64]

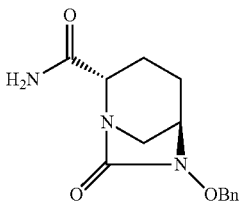

60 mg of (2S,5R)-2,5-dioxopyrrolidin-1-yl 6-(benzyloxy)-7-oxo-1,6-diazabicyclo[3.2.1]octane-2-carboxylate was dissolved in dehydrated dichloromethane (0.8 mL), followed by cooling to 0° C. 0.12 mL of concentrated aqueous ammonia was added to the reaction solution, followed by stirring at room temperature for 1 hour. Subsequently, water (10 mL) was added and the organic layer was fractionated, followed by sequential washing with water and saturated brine and drying over anhydrous magnesium sulfate. The residue resulting from concentration of the solvent under reduced pressure was applied to silica gel column chromatography (hexane/ethyl acetate=1/3), and subsequently crystallized with chloroform/hexane=1:3 to afford 30.4 mg of the title compound as a colorless crystalline powder.

[α]$^{20}_D$ −26.1° (c 0.498, MeOH); $^1$H NMR (400 MHz, CDCl$_3$, δ): 1.60 (m, 1H), 1.90-2.03 (m, 2H), 2.36 (m, 1H), 2.76 (d, J=11.6 Hz, 1H), 3.03 (d, J=11.6 Hz, 1H), 3.31 (s, 1H), 3.95 (d, J=7.6 Hz, 1H), 4.91 (s J=11.2 Hz, 1H), 5.06 (d, J=11.6 Hz, 1H), 5.45 (s, 1H), 6.56 (s, 1H), 7.26-7.44 (m, 5H); MS m/z: 276 (M+1).

Example 22

(2S,5R)-6-(Benzyloxy)-7-oxo-1,6-diazabicyclo[3.2.1]octane-2-carboxamide (F1-4)

[Chemical formula 65]

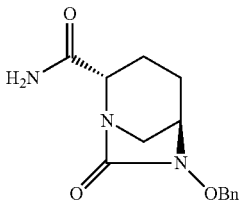

400 mg (1.44 mmol) of (2S,5R)-6-(benzyloxy)-7-oxo-1,6-diazabicyclo[3.2.1]octane-2-carboxylic acid was dissolved in dehydrated dichloromethane (14.4 mL), and 176 mg of triethylamine was added, followed by cooling to 0° C. 237 mg of isobutyl chloroformate was added to the mixture, followed by stirring at the same temperature for 20 minutes, 1.0 mL of concentrated aqueous ammonia was added to the reaction mixture, followed by stirring at room temperature for 1 hour. Subsequently, water (10 mL) was added and the organic layer was fractionated, followed by sequential washing with water and saturated brine and drying over anhydrous magnesium sulfate. The residue resulting from concentration of the solvent under reduced pressure was applied to silica gel column chromatography (hexane/ethyl acetate=1/3), and subsequently crystallized with chloroform/hexane=1:3 to afford 315 mg of the title compound as a colorless crystalline powder (yield 79%). Enantiomeric excess: 99.9% ee or more (CHIRALPAK AD-H, 4.6×150 mm, hexane/ethanol=4/1, UV 210 nm, flow rate 1 mL/min., retention time 16.2 min.).

Mp 169° C.; $[\alpha]^{20}_D$ –22.0°(c 1.26, MeOH); $^1$H NMR and MS were equivalent to those of the title compound of Example 21.

In powder X-ray diffraction diagram, the crystal of the title compound demonstrated characteristic peak patterns as shown in the following Table 11. For measurement, RINT 2100 from Rigaku Corporation was used as a powder X-ray diffraction device, in which measurement was conducted with CuKα1 as an X-ray source, a tube voltage of 40 kV, a tube current of 40 mA, a scan speed of 4°/min., and a scan range of 2θ=3 to 40°.

TABLE 13

Powder X-ray Diffraction of Compound (F1-4)

| Peak Position | | |
|---|---|---|
| 2θ (Cuka) | Spacing (d) Å | Relative Intensity I/I0 |
| 6.76 | 13.06 | 100 |
| 13.58 | 6.52 | 23 |
| 17.24 | 5.14 | 48 |
| 18.70 | 4.74 | 34 |
| 19.16 | 4.63 | 13 |
| 20.46 | 4.34 | 45 |
| 23.08 | 3.85 | 17 |
| 23.92 | 3.72 | 8 |

Example 23

(2S,5R)-1,6-Diazabicyclo[3.2.1]octane-2-carboxamide, 7-oxo-6-(sulfoxy)-monosodium salt (H)

Step 1: (2S,5R)-6-Hydroxy-7-oxo-1,6-diazabicyclo[3.2.1]octane-2-carboxamide (G)

[Chemical formula 66]

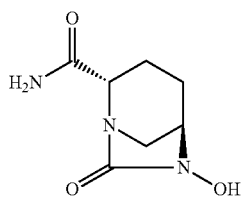

445 mg of (2S,5R)-6-(benzyloxy)-7-oxo-1,6-diazabicyclo[3.2.1]octane-2-carboxamide was dissolved in methanol (16 mL), and 80 mg of 10% palladium-carbon (50% water content) was added, followed by stirring for 0.75 hours under hydrogen atmosphere. The catalyst of the reaction mixture was filtered through celite, and the solvent was concentrated under reduced pressure and dried under vacuum to afford 357 mg of the title compound as a colorless solid (quantitative).

$[\alpha]^{20}_D$ –66.7°(c 1.22, MeOH); $^1$H NMR (400 MHz, CD$_3$OD, δ): 1.74 (m, 1H), 1.89 (m, 1H), 2.04 (m, 1H), 2.26 (m, 1H), 2.96 (d, J=11.6 Hz, 1H), 3.15 (m, 1H), 3.69 (s, 1H), 3.84 (d, J=8.0 Hz, 1H); MS m/z: 186 (M+1).

Step 2: (2S,5R)-1,6-Diazabicyclo[3.2.1]octane-2-carboxamide, 7-oxo-6-(sulfoxy)-monosodium salt (H)

[Chemical formula 67]

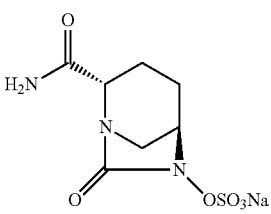

317 mg of (2S,5R)-6-hydroxy-7-oxo-1,6-diazabicyclo[3.2.1]octane-2-carboxamide was dissolved in dehydrated pyridine (17 mL), and 1360 mg of sulfur trioxide-pyridine complex was added, followed by stirring at room temperature for 20 hours. The solid in the reaction solution was filtered, the solvent of the filtrate was concentrated under reduced pressure, and the residue was dissolved in saturated aqueous sodium dihydrogen phosphate solution (30 mL), followed by washing with ethyl acetate (50 mL). 609 mg of tetrabutyl ammonium hydrogen sulfate was dissolved in the aqueous phase, followed by extraction with ethyl acetate (100 mL×4 times) and drying over anhydrous sodium sulfate, and the solvent was concentrated under reduced pressure. Tetrabutyl ammonium salt (crude yield 86%) obtained from subjecting the residue to silica gel column chromatography (dichloromethane/acetone=50/50) was dissolved in 50% aqueous acetone, applied to DOWEX 50W×8 (Na type, 150 mL) and eluted with water, and the active fraction was lyophilized to afford 338 mg of the title compound as a colorless solid (yield 80%). LC-MS purity 100%.

$[\alpha]^{20}_D$ –37.1°(c 0.496, H$_2$O); $^1$H NMR (400 MHz, D$_2$O, δ): 1.68 (m, 1H), 1.81 (m, 1H), 1.95 (m, 1H), 2.07 (m, 1H), 3.00 (d, J=12.4 Hz, 1H), 3.22 (d, J=12.0 Hz, 1H), 3.94 (d, J=7.6 Hz, 1H), 4.08 (s, 1H); MS m/z: 264 (M–1).

Example 24

(2R,5S)-1,6-Diazabicyclo[3.2.1]octane-2-carboxamide, 7-oxo-6-(sulfoxy)-monosodium salt (r)

Step 1: (2R/S,5S/R)-tert-Butyl 6-(benzyloxy)-7-oxo-1,6-diazabicyclo[3.2.1]octane-2-carboxylate

[Chemical formula 68]

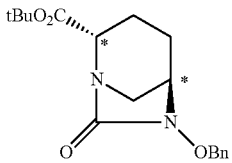

An aqueous hydrochloric acid solution of racemic 5-ketopiperidine-2-carboxylic acid obtained from the methods described in Non-Patent Document 5, Non-Patent Document 6 and Non-Patent Document 7 was benzyloxycarbonylated with benzyl chloroformate while maintaining pH at 10.5 with sodium hydroxide, subsequently the crude product was treated, in dehydrated dichloromethane, with tert-butylalcohol, 1-ethyl-3-(3-dimethylaminopropyl)carbodiimide hydrochloride and 4-dimethylaminopyridine, and the crude product was further reduced in methanol with sodium borohydride and column-purified to afford (2S/R,5S/R)-1-benzyl 2-tert-butyl 5-hydroxypiperidine-1,2-dicarboxylate, which was used to afford the title compound as a colorless solid according to Examples 1 to 6. Enantiomeric excess: 3% ee (CHIRALPAK AD-H, 4.6×150 mm, hexane/ethanol=2/1, UV 210 nm, flow rate 1 mL/min., retention time 4.2 min. (2R,5S), 7.9 min. (2S,5R)).

Mp 100° C.; $^1$H NMR and MS were equivalent to those of the title compound of Example 6.

Step 2: (2R,5S)-tert-Butyl 6-(benzyloxy)-7-oxo-1,6-diazabicyclo[3.2.1]octane-2-carboxylate (p)

[Chemical formula 69]

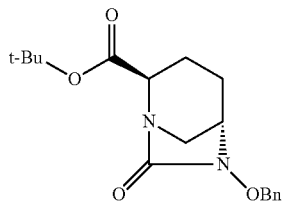

30.3 g of (2R/S,5S/R)-tert-butyl 6-(benzyloxy)-7-oxo-1,6-diazabicyclo[3.2.1]octane-2-carboxylate was applied to chiral column chromatography (CHIRAL PAK IA, methanol/acetonitrile=95/5), and the active fraction corresponding to the first peak was collected to afford 13.9 g of the title compound as a colorless solid (yield 46%). Enantiomeric excess: 99.9% ee or more (CHIRALPAK AD-H, 4.6×150 mm, hexane/ethanol=2/1, UV 210 nm, flow rate 1 mL/min., retention time 4.2 min.).

Mp 84° C.; $[\alpha]^{20}_D$ −6.1°(c 0.83, CHCl$_3$); $^1$H NMR and MS were equivalent to those of the title compound of Example 6.

Step 3: Cyclohexylamine salt of (2R,5S)-6-(benzyloxy)-7-oxo-1,6-diazabicyclo[3.2.1]octane-2-carboxylic acid (F1-1a)

[Chemical formula 70]

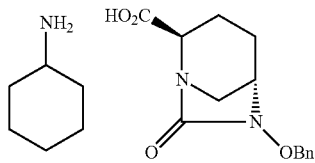

To a solution of 3.34 g (10.0 mmol) of (2R,5S)-tert-butyl 6-(benzyloxy)-7-oxo-1,6-diazabicyclo[3.2.1]octane-2-carboxylate in dichloromethane (25 mL), under argon atmosphere at 0° C., was added trifluoroacetic acid (25 mL), followed by raising the temperature to room temperature and allowing to react for 4 hours. After the reaction mixture was concentrated, the resulting residue was diluted with ethyl acetate, subsequently washed sequentially with water and saturated brine and dried over anhydrous magnesium sulfate, and the solvent was distilled off under reduced pressure. The resulting residue was dissolved in ethyl acetate (10 mL), and a solution of 256 mg of cyclohexylamine in diethylether was added at room temperature, followed by aging at 0° C. for 1 hour. The generated precipitate was filtered off, and the filter cake was washed with diethylether, followed by drying under reduced pressure to afford 3.36 g of the title compound as a colorless crystalline powder (yield 89%).

$[\alpha]^{20}_D$+35.7°(c 0.51, H$_2$O); $^1$H NMR and MS were equivalent to those of the title compound of Example 8.

Step 4: (2R,5S)-6-(Benzyloxy)-7-oxo-1,6-diazabicyclo[3.2.1]octane-2-carboxylic acid (q)

[Chemical formula 71]

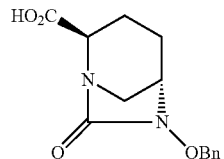

Cyclohexylamine salt 750 mg of (2R,5S)-6-(benzyloxy)-7-oxo-1,6-diazabicyclo[3.2.1]octane-2-carboxylic acid was dissolved in saturated aqueous sodium dihydrogen phosphate solution, followed by extraction three times with ethyl acetate, and the combined organic layer was washed with saturated brine and subsequently dried over anhydrous magnesium sulfate. The solvent was distilled off under reduced pressure to afford 507 mg of the title compound as a colorless oil (yield 91.5%). Enantiomeric excess: 98.6% ee. (CHIRALPAK AD-H, 4.6×150 mm, trifluoroacetic acid/hexane/ethanol=0.1/80/20, UV 210 nm, flow rate 1 mL/min., retention time 6.2 min.).

$[\alpha]^{20}_D$ −11.1°(c 0.90, CHCl$_3$); $^1$H NMR and MS were equivalent to those of the title compound of Example 9.

Step 5: (2R,5S)-6-(Benzyloxy)-7-oxo-1,6-diazabicyclo[3.2.1]octane-2-carboxamide

[Chemical formula 72]

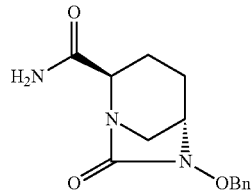

230 mg (0.84 mmol) of (2R,5S)-6-(benzyloxy)-7-oxo-1,6-diazabicyclo[3.2.1]octane-2-carboxylic acid was dissolved in dehydrated dichloromethane (4.2 mL), and 110 mg of triethylamine was added, followed by cooling to 0° C. 137 mg of isobutyl chloroformate was added to the mixture, followed by stirring at the same temperature for 20 minutes.

0.6 mL of aqueous ammonia was added to the reaction mixture, followed by stirring at room temperature for 1 hour. Subsequently, water (10 mL) was added and the organic layer was aliquoted, followed by sequential washing with water and saturated brine and drying over anhydrous magnesium sulfate. The residue resulting from concentration of the solvent under reduced pressure was applied to silica gel column chromatography (hexane/ethyl acetate=1/3), and subsequently crystallized with chloroform/hexane=1:3 to afford 202 mg of the title compound as a colorless crystalline powder (yield 87%). Enantiomeric excess: 99.9% ee or more (CHIRALPAK AD-H, 4.6×150 mm, hexane/ethanol=4/1, UV 210 nm, flow rate 1 mL/min., retention time 10.3 min.).

$[\alpha]^{20}_D$+24.5°(c 0.61, MeOH); $^1$H NMR and MS were equivalent to those of the title compound of Example 22.

Step 6: (2R,5S)-6-Hydroxy-7-oxo-1,6-diazabicyclo[3.2.1]octane-2-carboxamide (r)

[Chemical formula 73]

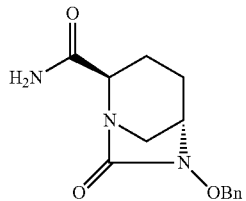

190 mg of (2S,5R)-6-(benzyloxy)-7-oxo-1,6-diazabicyclo[3.2.1]octane-2-carboxamide was dissolved in methanol (6.9 mL), and 40 mg of 10% palladium carbon (50% water content) was added, followed by stirring for 1.5 hours under hydrogen atmosphere. The catalyst of the reaction mixture was filtered through celite, and the solvent was concentrated under reduced pressure and dried under vacuum to afford 126 mg of the title compound as a colorless solid (quantitative).

$[\alpha]^{20}_D$−55.7°(c 0.52, MeOH); $^1$H NMR and MS were equivalent to those of the title compound of Example 23, Step 1.

Step 7: (2R,5S)-1,6-Diazabicyclo[3.2.1]octane-2-carboxamide, 7-oxo-6-(sulfoxy)-monosodium salt (s)

[Chemical formula 74]

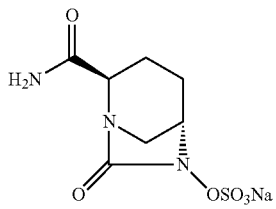

112 mg of (2R,5S)-6-hydroxy-7-oxo-1,6-diazabicyclo[3.2.1]octane-2-carboxamide was dissolved in dehydrated pyridine (6 mL), and 481 mg of sulfur trioxide.pyridine complex was added, followed by stirring at room temperature for 20 hours. The solid of the reaction solution was filtered, the solvent of the filtrate was concentrated under reduced pressure, and the residue was dissolved in saturated aqueous sodium dihydrogen phosphate solution (30 mL) and washed with ethyl acetate (50 mL). 190 mg of tetrabutyl ammonium hydrogen sulfate was dissolved in the aqueous phase, followed by stirring for 10 minutes. The reaction solution was extracted with ethyl acetate (100 mL×5 times) and dried over anhydrous sodium sulfate, and subsequently the solvent was concentrated under reduced pressure. Tetrabutyl ammonium salt (crude yield 85%) obtained by subjecting the residue to silica gel column chromatography (dichloromethane/acetone=50/50) was dissolved in 50% aqueous acetone, applied to DOWEX5WX8 (Na type, 61 mL) and eluted with water, and the active fraction was lyophilized to afford 109 mg of the title compound as a colorless solid (yield 63%). LC-MS purity 100%.

$[\alpha]^{20}_D$+38.1°(c 0.496, H$_2$O); $^1$H NMR and MS were equivalent to those of the title compound of Example 22, Step 2.

Example 25

β-lactamase enzyme inhibitory activity of the compounds produced in Examples 23 and 24 and antibacterial activity of PIPC in combination with the compounds were determined. The structural formulae of the test compound are as shown in the following Table 14.

TABLE 14

| Compound name | Structural formula |
|---|---|
| Tazobactam (TAZ) | |
| Example 23 | |
| Example 24 | |

β-Lactamase Enzyme Inhibitory Activity

Using *P. aeruginosa* PAO1 genome as a template, a DNA for encoding an AmpC β-lactamase domain excluding a signal peptide was amplified with PCR. This PCR product was incorporated into pET-28b(+)vector (Merck), introduced into *E. coli* BL21 (Merck), and, under induction of 1 mM isopropyl-β-D-(−)-thiogalactopyranoside (Nacalai Tesque), cultured overnight at 20° C. to express AmpC. After the bacterial cell was collected, AmpC was purified from the cell extract obtained by ultrasonic treatment, using CM Sepharose Fast Flow (GE Healthcare) and HiTrap Heparin HP (GE Healthcare) at 4° C.

For the measurement of β-lactamase inhibitory activity, 100 μM (final concentration) nitrocefin (Oxoid) was used as a substrate, and 2.5% DMSO, 10 μg/mL bovine serum derived albumin (Sigma-Aldrich) and 50 mM phosphate buffer at pH 7.0 were used as a reaction solution. To each well of a 96-well plate were added test compounds (compounds shown in Table 14) and AmpC (final concentration 0.5 nM), followed by pre-incubation at 30° C. for 10 minutes. Nitrocefin was added to each well to be mixed therein, followed by incubation at 30° C. for 20 minutes, and Multiskan Ascent (Thermo Fisher Scientific) was used to measure 492 nm wavelength, thereby measuring nitrocefin hydrolytic activity of AmpC, to determine enzyme inhibitory activity. As a control, a reaction solution excluding AmpC was prepared, and the concentration of a test compound exhibiting 50% inhibition was determined to be $IC_{50}$ value. The results were as shown in Table 15.

TABLE 15

Inhibitory activity of test compound against AmpC

| Compound name | $IC_{50}$ value (μM) |
|---|---|
| TAZ | 0.95 |
| Example 23 | 0.65 |
| Example 24 | >30 |

Combinatorial Effect

The combinatorial effect of the test compound with a β-lactam agent against bacteria was evaluated using AmpC constitutive expression strain selected from *P. aeruginosa* PAO1 through agent exposure. Using piperacillin (PIPC, Sigma-Aldrich) as a β-lactam agent, measurement was conducted by agar plate dilution process in which minimal inhibitory concentration (MIC) of PIPC is based on Clinical and Laboratory Standards Institute (CLSI process). That is, an agara plate containing 4 μg/mL (final concentration) of test compound and PIPC at each concentration in Mueller-Hinton agar (Becton, Dickinson and Company) was made, and bacteria cultured overnight in cation-adjusted Muller-Hinton broth (Becton, Dickinson and Company) were adjusted in the same medium so as to have $10^4$ CFU/spot and inoculated on a plate containing an agent. This plate containing an agent was cultured overnight at 35° C., and the minimum agent concentration in which no growth of bacteria is observed was determined to be MIC. The results were as shown in Table 16.

TABLE 16

Combinatorial antibacterial activity when using in combination with 4 μg/mL of test compound against *P. aeruginosa* PAO1 variant, which constitutively expresses AmpC

| Compound name | MIC of PIPC (μM/ml) |
|---|---|
| alone | 64 |
| TAZ | 64 |
| Example 23 | 4 |
| Example 24 | 64 |

The invention claimed is:

1. An optically active (2S,5R)-7-oxo-1,6-diazabicyclo[3.2.1]octane-2-carboxylic acid compound defined by the following formula (F):

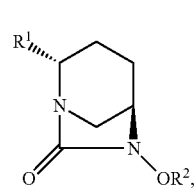

wherein $R^1$ represents $CO_2M$ or $CONH_2$;
M represents an inorganic cation selected from the group consisting of sodium, potassium, lithium and calcium or an organic cation selected from the group consisting of trimethylamine, triethylamine, dicyclohexylamine, tetramethylammonium, tetraethylammonium, tetrabutylammonium and triethylbenzylammonium; and
$R^2$ represents a benzyl group or an allyl group.

2. A process for preparing the compound defined by the formula (F) according to claim 1, which comprises subjecting a compound represented by formula (E) below to an intramolecular urea formation, and then subjecting the resultant compound represented by formula (F1) below to at least one of the steps (a) to (c) below:

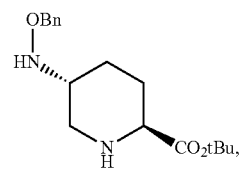

wherein Bn represents a benzyl group, and tBu represents a tert-butyl group;

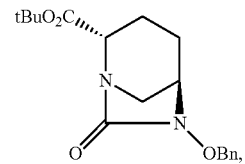

wherein Bn represents a benzyl group, and tBu represents a tert-butyl group;

step (a) for converting the compound of the formula (F1) to a form of a salt of an inorganic cation or an organic cation,
step (b) for treating the compound of the formula (F1) with an acid to convert the compound of the formula (F1) to a free acid, and then
performing a carbamoylation for the carboxylic acid group of the free acid,
step (c) for removing the benzyl group of the benzyloxy group at the 6-position, of the formula (F1) and then converting the group at the 6-position to an allyloxy.

3. The compound according to claim 1, wherein the compound is (2S,5R)-6-(benzyloxy)-7-oxo-1,6-diazabicyclo[3.2.1]octane-2-carboxamide.

4. The compound according to claim 1, wherein $R^1$ is $CO_2M$, and M is the inorganic cation.

5. The compound according to claim 1, wherein $R^1$ is $CO_2M$, and M is the organic cation.

6. The compound according to claim 1, wherein R¹ is CONH$_2$.

7. A process for preparing the compound defined by the following formula (F)

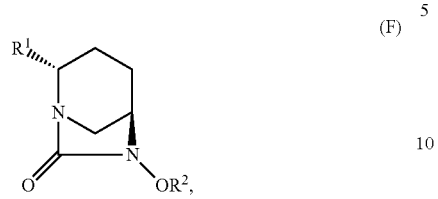

(F)

wherein R¹ represents CO$_2$R, CO$_2$M, or CONH$_2$,
wherein R represents an allyl group or a benzyl group, and
M represents a hydrogen atom, an inorganic cation, or an organic cation; and
R² represents a benzyl group or an allyl group,
the process comprising
subjecting a compound represented by formula (E) below to an intramolecular urea formation, and then subjecting the resultant compound represented by formula (F1) below to at least one of the steps (a) to (g) below:

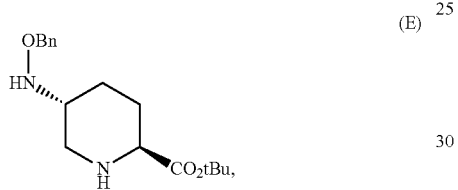

(E)

wherein Bn represents a benzyl group, and tBu represents a tert-butyl group;

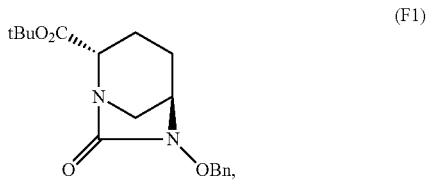 [SMILES: CC(C)(C)OC(=O)[C@@H]1CC[C@@H]2CN1C(=O)N2OCc1ccccc1]

(F1)

wherein Bn represents a benzyl group, and tBu represents a tert-butyl group;

step (a) for cleaving the ester group of the formula (F1), step (b) for converting the compound of the formula (F1) to a form of a salt of an inorganic cation or an organic cation, step (c) for treating the compound of the formula (F1) with an acid to convert the compound of the formula (F1) to a free acid, step (d) for performing a carbamoylation for the carboxylic acid group of the formula (F1), step (e) for converting the carboxylic acid group of the formula (F1) to an ester, step (f) for removing the benzyl group of the benzyloxy group at the 6-position, of the formula (F1) and step (g) for converting the group at the 6-position to an allyloxy.

* * * * *